United States Patent
Huang et al.

(10) Patent No.: US 11,471,503 B2
(45) Date of Patent: Oct. 18, 2022

(54) USE OF KOR AGONIST IN COMBINATION WITH MOR AGONIST IN PREPARING DRUG FOR TREATING PAIN

(71) Applicant: JIANGSU HENGRUI MEDICINE CO., LTD., Jiangsu (CN)

(72) Inventors: Xiaoxing Huang, Jiangsu (CN); Guoqing Cao, Jiangsu (CN); Changyong Yang, Jiangsu (CN); Lianshan Zhang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 115 days.

(21) Appl. No.: 16/767,523

(22) PCT Filed: Dec. 5, 2018

(86) PCT No.: PCT/CN2018/119313
§ 371 (c)(1),
(2) Date: May 27, 2020

(87) PCT Pub. No.: WO2019/109937
PCT Pub. Date: Jun. 13, 2019

(65) Prior Publication Data
US 2020/0368309 A1 Nov. 26, 2020

(30) Foreign Application Priority Data
Dec. 6, 2017 (CN) .......................... 201711272869.1

(51) Int. Cl.
*A61K 38/07* (2006.01)
*A61K 31/4433* (2006.01)
(Continued)

(52) U.S. Cl.
CPC .......... *A61K 38/07* (2013.01); *A61K 31/4433* (2013.01); *A61P 23/00* (2018.01); *A61P 25/04* (2018.01)

(58) Field of Classification Search
CPC ...... A61K 38/07; A61K 31/4433; A61P 23/00
See application file for complete search history.

(56) References Cited

U.S. PATENT DOCUMENTS

2011/0212882 A1 9/2011 Schteingart et al.

FOREIGN PATENT DOCUMENTS

| CA | 3000761 A1 | 4/2017 |
| CN | 103702561 A | 4/2014 |

(Continued)

OTHER PUBLICATIONS

Dooley, Selective Ligands for the m, d, and k Opioid Receptors Identified from a Single Mixture Based Tetrapeptide Positional Scanning Combinatorial Library*, Journal of Biological Chemistry; 273, 30, 18848-18856. (Year: 1998).*

(Continued)

*Primary Examiner* — Kevin S Orwig
*Assistant Examiner* — John Michael Cronin
(74) *Attorney, Agent, or Firm* — Ice Miller LLP

(57) ABSTRACT

Disclosed is the use of a KOR agonist in combination with a MOR agonist in preparing a drug for treating pain. The KOR agonist is selected from a compound as shown in the general formula (I), and the MOR agonist is selected from a compound as shown in the general formula (II), wherein the definitions of each substituent in the general formula (I) and (II) are the same as defined in the description.

(Continued)

US 11,471,503 B2
Page 2

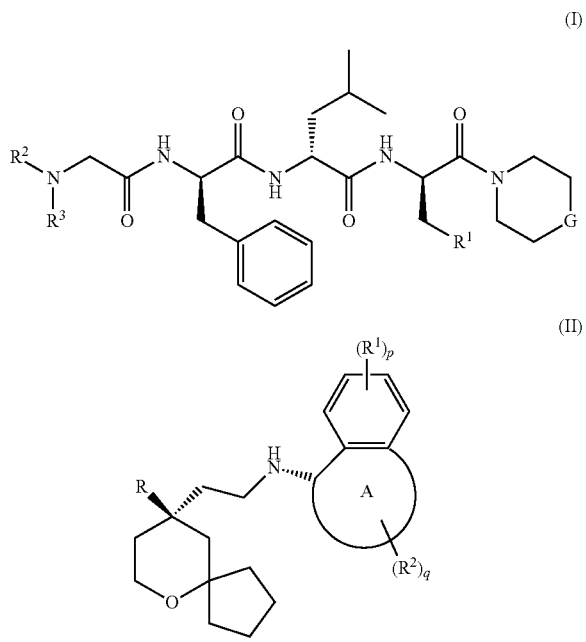

20 Claims, 1 Drawing Sheet

(51) Int. Cl.
 *A61P 25/04* (2006.01)
 *A61P 23/00* (2006.01)

(56) References Cited

FOREIGN PATENT DOCUMENTS

| | | | |
|---|---|---|---|
| CN | 104271552 A | 1/2015 | |
| TW | 201601743 A | 1/2016 | |
| WO | 2008057608 A2 | 5/2008 | |
| WO | 2008060552 A2 | 5/2008 | |
| WO | WO 2008/057608 A2 * | 5/2008 | ............. C07K 5/107 |
| WO | 2012129495 A1 | 9/2012 | |
| WO | 2015065867 A2 | 5/2015 | |
| WO | 2016073443 A2 | 5/2016 | |
| WO | 2017063509 A1 | 4/2017 | |
| WO | 2017211272 A1 | 12/2017 | |
| WO | 2018103624 A1 | 6/2018 | |

OTHER PUBLICATIONS

Martinez-Mayorga, Ligand/kappa-opioid receptor interactions: Insights from the X-ray crystal structure, European Journal of Medicinal Chemistry;66, 114-121. (Year: 2013).*

Joshi, Alanine scan of the opioid peptide dynorphin B amide, Biopolymers; 108(5); DOI: 10.1002/bip.23026 (Year: 2017).*

Spetea, Selective κ receptor partial agonist HS666 produces potent antinociception without inducing aversion after i.c.v. administration in mice; British Journal of Pharmacology; 174, 2444-2456 (Year: 2017).*

Extended European Search Report dated Aug. 3, 2021 in European Application No. 18885338.6.

Lu, Hannah P., et al., "Interactions between Mu and Kappa Opioid Receptor Agonists: Antinociceptive and Adverse Effects in Rats," FASEB Journal, vol. 31, No. Suppl. 1, pp. 985.17, Apr. 2017.

Sakakihara, Manabu, et al., "Effects of Intrathecal kappa-Opioid Receptor Agonist on Morphine-Induced Itch and Antinociception in Mice," Regional Anesthesia and Pain Medicine, vol. 41, No. 1, pp. 69-74, Jan. 2016.

Negus, S. Stevens, et al., "Mu/Kappa Opioid Interactions in Rhesus Monkeys: Implications for Analgesia and Abuse Liability," Experimental and Clinical Psychopharmacology, vol. 16, No. 5, pp. 386-399, Oct. 2008.

Rech, Richard H., et al., "Effects of combined opioids on pain and mood in mammals," Pain Research and Treatment 2012, vol. 2012, Article ID 145965, pp. 1-11, Jan. 2, 2012.

Fujita-Hamabe, Wakako et al., "Involvement of kappa opioid receptors in the formalin-induced inhibition of analgesic tolerance to morphine via suppression of conventional protein kinase C activation," Journal of Pharmacy and Pharmacology, 2010, 62(8), 995-1002.

Gavva, Narender R. et al., "Transient receptor potential melastatin 8 (TRPM8) channels are involved in body temperature regulation," Molecular Pain, 2012, 8(1), 10.

Kiviranta, Päivi H. et al., "N-(3-(4-Hydroxyphenyl)-propenoyl)-amino acid tryptamides as SIRT2 inhibitors," Bioorganic & Medicinal Chemistry Letters, 2007, 7(9), 2448-2451.

Holvey, Rhian S. et al., "Selective Targeting of the TPX2 Site of Importin-α Using Fragment-Based Ligand Design," ChemMedChem, 2015, 10(7), 1232-1239.

Czekelius, Constantin et al., "Catalytic Enantioselective Conjugate Reduction of β,β-Disubstituted Nitroalkenes," Angewandte Chemie, International Edition, 2003, 42(39), 4793-4795.

Liang, Chungen et al., "Efficient Diastereoselective Intermolecular Rhodium-Catalyzed C-H Amination," Angewandte Chemie, International Edition, 45(28), 4641-4644, 2006.

International Search Report, International Application No. PCT/CN2018/119313, dated Mar. 7, 2019.

* cited by examiner

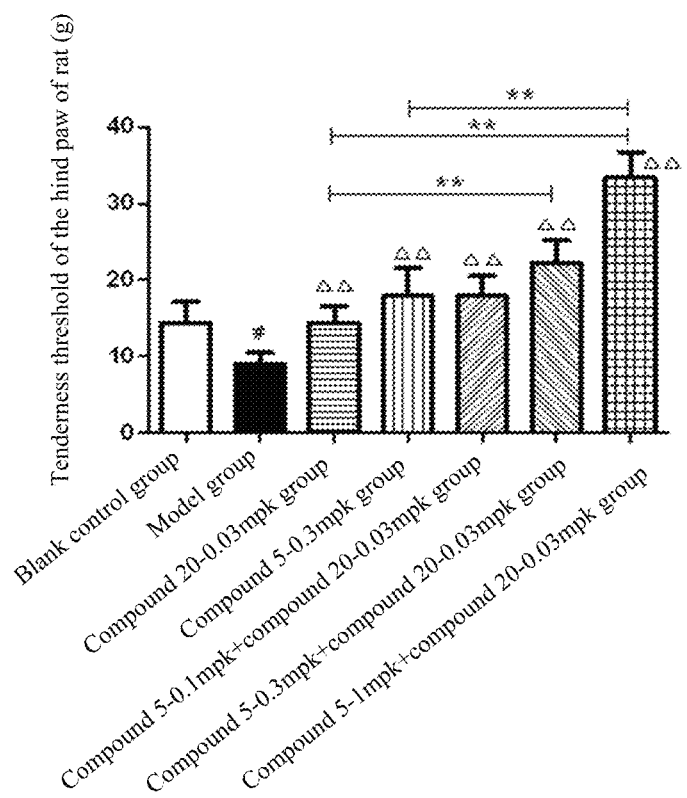

USE OF KOR AGONIST IN COMBINATION WITH MOR AGONIST IN PREPARING DRUG FOR TREATING PAIN

CROSS-REFERENCE TO RELATED APPLICATIONS

This application is a Section 371 of International Patent Application No. PCT/CN2018/119313, filed Dec. 5, 2018, which was published in the Chinese language on Jun. 13, 2019, under International Publication No. WO 2019/109937 A1, which claims priority under 35 U.S.C. § 119(b) to Chinese Patent Application No. 201711272869.1, filed Dec. 6, 2017, the disclosure of all of which are incorporated herein by reference in their entireties.

FIELD OF THE INVENTION

The present invention belongs to the field of medicine, and relates to a use of a combination of a KOR agonist and a MOR agonist in the preparation of a medicament for alleviating and/or treating pain.

BACKGROUND OF THE INVENTION

Pain refers to a person's functional or substantial feelings. The classification of pain is complicated. According to the etiology, pain is mainly classified into traumatic pain, pathological pain, pain caused by metabolic diseases, neuropathic pain, pain caused by tissue and organ malformation, psychological pain, and pain caused by combined factors. According to the course, pain is mainly classified into transient pain, acute pain and chronic pain. According to the degree, pain is classified into faint pain, mild pain, serious pain and severe pain. According to the anatomy, pain is mainly classified into headache, maxillofacial pain, cervical and occipital pain, neck and shoulder pain, upper limb pain, chest pain, abdominal pain, and lumbocrural pain. According to the location and cause, pain is classified into peripheral pain, central pain and psychological pain. The causes of pain diseases are complicated, and the symptoms are different. The degree of tolerance to pain and the response to treatment vary greatly between patients. At present, the clinically used drugs for treating pain mainly include anti-inflammatory analgesics, narcotic analgesics, local anesthetics, anti-epileptic drugs, anti-depressants and the like. Although there are many drugs for analgesia, there are still problems such as constipation, respiratory depression, sedation and lethargy, nausea and vomiting, acute poisoning, physical dependence and drug resistance, psychological dependence and the like.

Opioids are commonly used analgesics in clinical practice, and especially play an important role in treating patients with severe pain and advanced cancer. Opioids produce an analgesic effect primarily through acting on the opioid receptor. The opioid receptor is a member of the G protein-coupled receptor superfamily, and participates in a variety of physiological activities such as analgesia, inhibition of gastrointestinal motility, respiratory depression, myocardial protection, immune response and the like. In general, the opioid receptor can be divided into four subtypes: μ opioid receptor (MOR), δ opioid receptor (DOR), κ opioid receptor (KOR), and opioid receptor like-1 (ORL-1). Studies find that MOR receptor has the strongest binding ability to morphin-1. Therefore, the opioid analgesics used in clinical practice are mainly MOR agonists, such as morphine, tramadol, fentanyl, oxycodone and the like. However, long-term use of these drugs can cause severe side effects such as analgesia tolerance, dependence, addiction and the like. The MOR agonists currently in phase III clinical studies include TRV-130, which is developed by Trevena Inc. WO2017063509 discloses a novel MOR agonist, of which the structure is shown as follows:

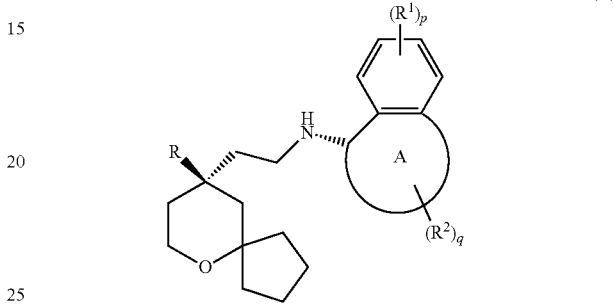

WO2012129495 discloses a MOR agonist with a similar structure.

The study of the structure and function of various subtypes of opioid receptors breaks the previous understanding that a highly selective ligand targeting a single opioid receptor will have a high activity and low toxicity side effect. At present, more studies find that a highly selective agonist can enhance side effects instead of reducing them. Studies find that there are different degrees of structural or functional interactions between different subtypes of opioid receptors, which participate together in physiological activities such as analgesia and the like. The study by Fujita-Hamabe et al. (Journal of Pharmacy and Pharmacology, 2010, 62(8): 995-1002) demonstrates that KOR can inhibit the desensitization of MOR, accelerate the intracellular circulation of MOR to increase surface receptor, and reduce the activity of protein kinase C, thereby inhibiting the analgesic tolerance and dependence of MOR agonists. The study by Cunha T M et al. ([J]. Molecular pain, 2012, 8(1): 10) finds that the activation of peripheral MOR can inhibit inflammatory pain and prostatin E2-induced progressive hyperalgesia. It has been reported that the activation of KOR can also inhibit inflammatory hyperalgesia, and its mechanism may involve the activation of PI3K γ/AKT signaling pathway through nNOS/NO signaling pathway. Rong L I U et al. ([J]. China Pharmaceuticals, 2016, 25(22): 41-44) report the analgesia and sedation effect of the KOR agonist nalbuphine and MOR agonist sufentanil after elderly total hip arthroplasty, demonstrating that the combined administration has a better analgesic effect than single administration, and significantly reduces adverse reactions such as nausea, vomiting, skin itch and the like.

Patent application PCT/CN2017/087328 provides a novel KOR agonist. It has an extremely low distribution in brain tissue, a smaller effect on the central nervous system, and little effect on sodium in serum. It is not easily addicted, and has a higher safety. Its structure is shown as follows:

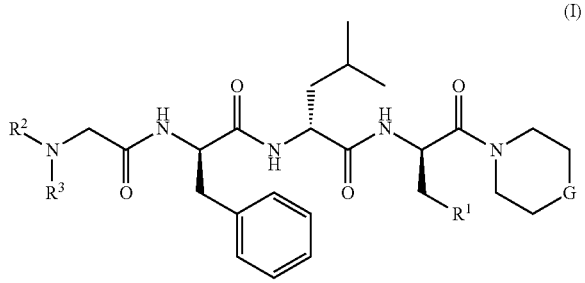

WO2008060552 discloses a KOR agonist with a similar structure, and its use for analgesia in combination with other opioid receptor agonists, NSAIDs and anti-depressants. WO2016073443 discloses a use of a similar KOR agonist for treating surgical pain and sclerous tissue pain. WO2008057608 discloses a use of a combination of a similar KOR agonist and a MOR agonist for treating pain as well as the decrease of the dose of MOR agonist and adverse reactions. WO2015065867 discloses a use of a similar KOR agonist administrated after administration of a MOR agonist for reducing the vomiting induced by the MOR agonist. In summary, the combined administration of a KOR agonist and a MOR agonist is a potential method for alleviating and/or treating pain. The present invention provides a use of a combination of a novel structure of a KOR agonist and a MOR agonist in the preparation of a medicament for alleviating and/or treating pain.

SUMMARY OF THE INVENTION

The technical problem to be solved by the present invention is to provide a use of a combination of a KOR agonist and a MOR agonist in the preparation of a medicament for alleviating and/or treating pain.

The KOR agonist is a compound of formula (I) having the following structure:

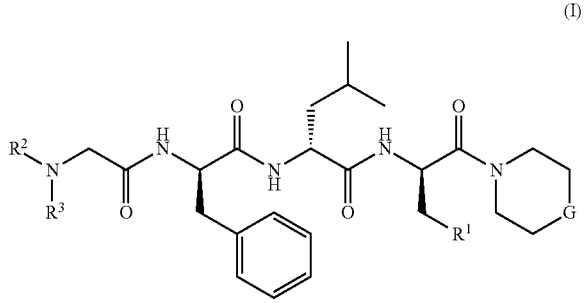

(I)

or a tautomer, mesomer, racemate, enantiomer, diastereomer thereof, or a mixture thereof, or a pharmaceutically acceptable salt thereof,
wherein:
G is selected from the group consisting of O, $-NR^4$ and $-CR^5R^6$;
$R^1$ is selected from the group consisting of hydrogen, alkyl, alkoxy, haloalkyl, halogen, amino, nitro, hydroxy, cyano, cycloalkyl, heterocyclyl, aryl, heteroaryl, $-OR^7$, $-C(O)R^7$, $-C(O)OR^7$, $-S(O)_mR^7$ and $-NR^8R^9$, wherein the alkyl, haloalkyl, cycloalkyl, heterocyclyl, aryl and heteroaryl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^2$ is selected from the group consisting of hydrogen, alkyl, alkoxy, haloalkyl, cycloalkyl, cycloalkylalkyl, heterocyclyl, heterocyclylalkyl, aryl, arylalkyl, heteroaryl, heteroarylalkyl, $-OR^7$, $-C(O)R^7$ and $-C(O)OR^7$, wherein the alkyl, haloalkyl, cycloalkyl, cycloalkylalkyl, heterocyclyl, heterocyclylalkyl, aryl, arylalkyl, heteroaryl and heteroarylalkyl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^3$ is selected from the group consisting of hydrogen, alkyl, alkoxy, haloalkyl, cycloalkyl, cycloalkylalkyl, heterocyclyl, heterocyclylalkyl, aryl, arylalkyl, heteroaryl, heteroarylalkyl, $-OR^7$, $-C(O)R^7$ and $-C(O)OR^7$, wherein the alkyl, haloalkyl, cycloalkyl, cycloalkylalkyl, heterocyclyl, heterocyclylalkyl, aryl, arylalkyl, heteroaryl and heteroarylalkyl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^4$ is selected from the group consisting of hydrogen, alkyl, haloalkyl, cycloalkyl, alkoxy, hydroxyalkyl, amino, alkoxycarbonyl, heterocyclyl, aryl, heteroaryl, $-OR^7$, $-C(O)R^7$, $-C(O)OR^7$, $-S(O)_mR^7$, $-NR^8R^9$ and $-NHC(O)NR^8R^9$, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

$R^5$ and $R^6$ are each independently selected from the group consisting of hydrogen, alkyl, alkoxy, hydroxyalkyl, hydroxy, amino, alkoxycarbonyl, cycloalkyl, heterocyclyl, aryl, heteroaryl, $-OR^7$, $-C(O)R^7$, $-C(O)OR^7$, $-S(O)_mR^7$, $-NR^8R^9$ and $-NHC(O)NR^8R^9$, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

$R^7$ is selected from the group consisting of hydrogen, alkyl, amino, alkoxy, hydroxyalkyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, nitro, cyano, alkoxy, hydroxyalkyl, cycloalkyl, heterocyclyl, aryl and heteroaryl;

$R^8$ and $R^9$ are each independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl; and m is 0, 1 or 2.

Preferably, the KOR agonist is a compound of formula (I-A):

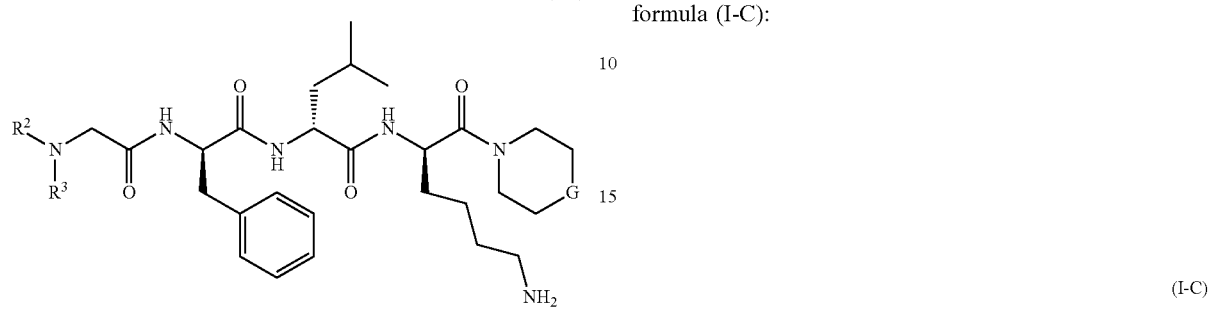

(I-A)

or a tautomer, mesomer, racemate, enantiomer, diastereomer thereof, or a mixture thereof, or a pharmaceutically acceptable salt thereof, wherein:

G, R² and R³ are as defined in the compound of formula (I).

Further preferably, the KOR agonist is a compound of formula (I-B):

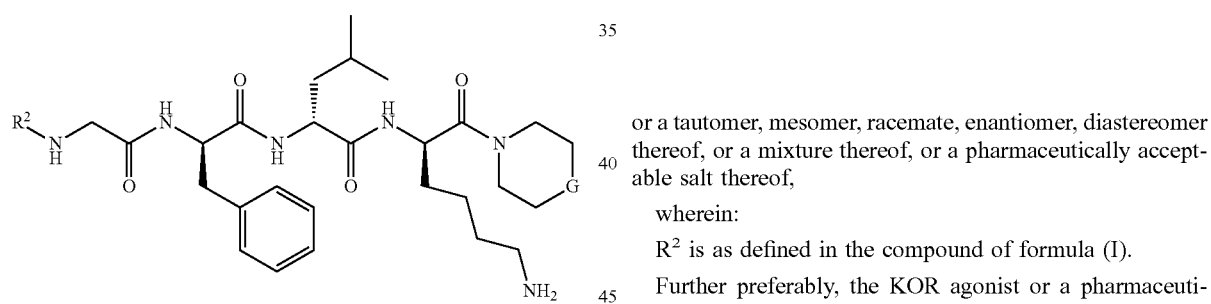

(I-B)

or a tautomer, mesomer, racemate, enantiomer, diastereomer thereof, or a mixture thereof, or a pharmaceutically acceptable salt thereof, wherein:

G and R² are as defined in the compound of formula (I).

Further preferably, the KOR agonist is a compound of formula (I-C):

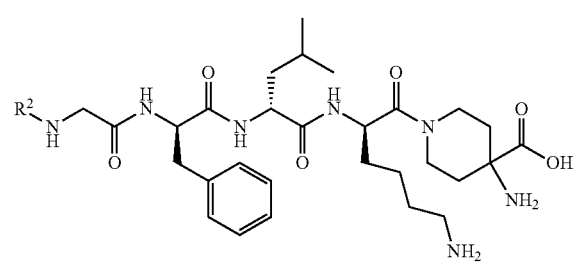

(I-C)

or a tautomer, mesomer, racemate, enantiomer, diastereomer thereof, or a mixture thereof, or a pharmaceutically acceptable salt thereof, wherein:

R² is as defined in the compound of formula (I).

Further preferably, the KOR agonist or a pharmaceutically acceptable salt thereof is selected from the group consisting of:

1

2
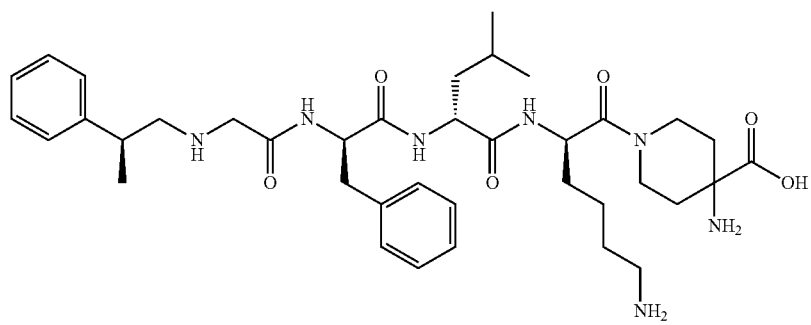
3
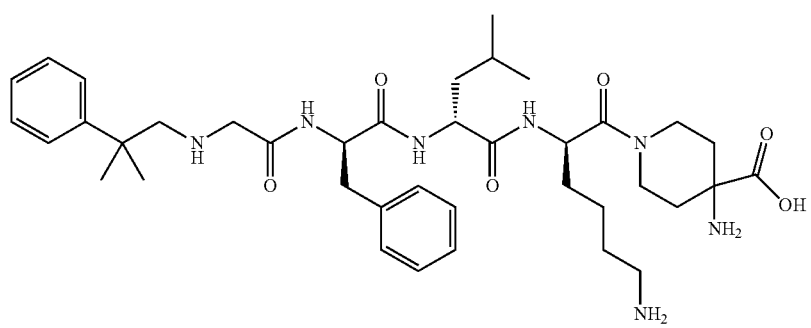
4
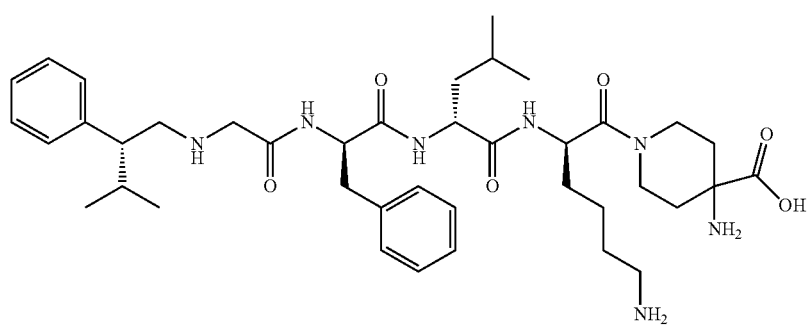
5
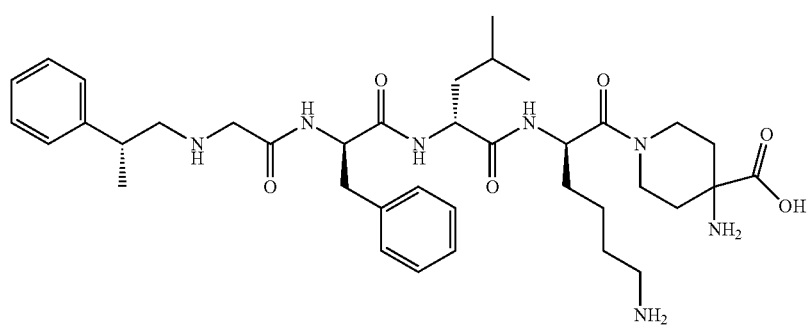
6
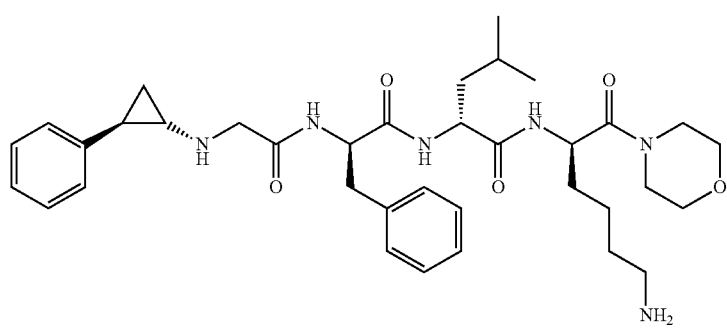

-continued
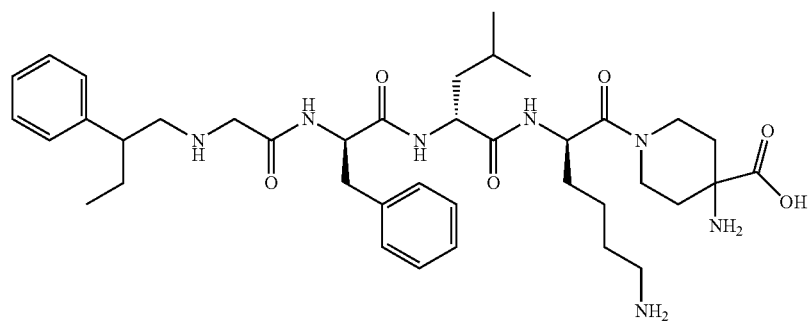
7
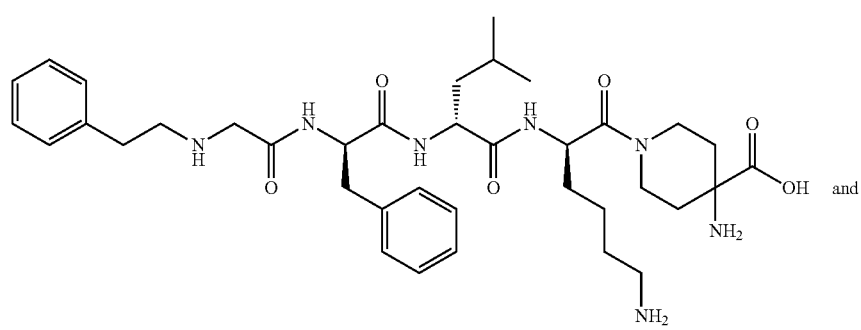
8
and
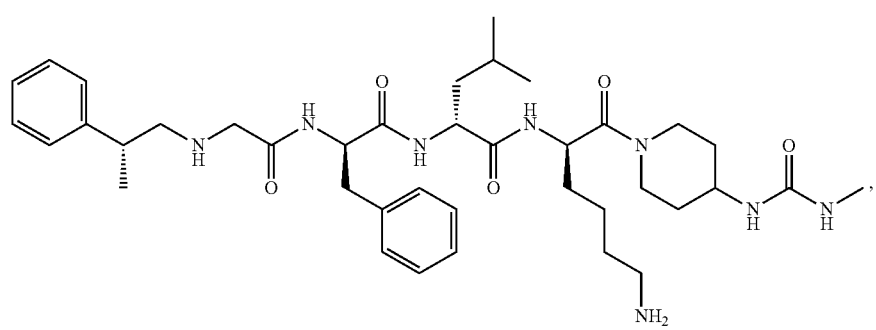
9
and preferably
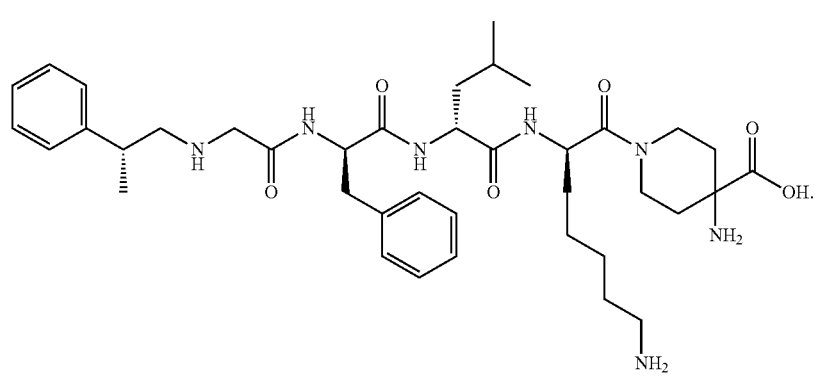
5

In the above preferred embodiments, the MOR agonist is a compound of formula (II):

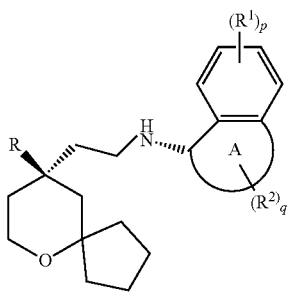

(II)

or a tautomer, mesomer, racemate, enantiomer, diastereomer thereof, or a mixture thereof, or a pharmaceutically acceptable salt thereof,
wherein:
ring A is selected from the group consisting of cycloalkyl and heterocyclyl;
R is selected from the group consisting of aryl and heteroaryl, wherein the aryl and heteroaryl are each optionally substituted by one or more substituents selected from the group consisting of alkyl, haloalkyl, halogen, amino, nitro, cyano, alkoxy, haloalkoxy, hydroxyalkyl, cycloalkyl, heterocyclyl, aryl, heteroaryl, —$OR^3$, —$C(O)R^3$, —$C(O)OR^3$, —$S(O)_mR^3$ and —$NR^4R^5$;
each $R^1$ is identical or different and each is independently selected from the group consisting of hydrogen, alkyl, alkoxy, haloalkyl, halogen, amino, nitro, hydroxy, cyano, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, haloalkyl, cycloalkyl, heterocyclyl, aryl and heteroaryl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;
each $R^2$ is identical or different and each is independently selected from the group consisting of hydrogen, alkyl, alkoxy, haloalkyl, halogen, amino, nitro, hydroxy, cyano, oxo, alkenyl, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, alkoxy, alkenyl, haloalkyl, cycloalkyl, heterocyclyl, aryl and heteroaryl are each optionally substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl and heteroaryl;
or two $R^2$ are taken together to form a cycloalkyl or heterocyclyl, wherein the cycloalkyl or heterocyclyl is optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;
$R^3$ is selected from the group consisting of hydrogen, alkyl, deuterated alkyl, amino, alkoxy, hydroxyalkyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, nitro, cyano, alkoxy, hydroxyalkyl, cycloalkyl, heterocyclyl, aryl and heteroaryl;

$R^4$ and $R^5$ are each independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;
p and q are each independently 0, 1, 2, 3 or 4; and
m is 0, 1 or 2.
Preferably, the MOR agonist is a compound of formula (II-B):

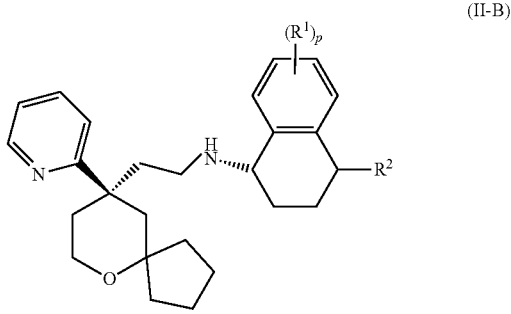

(II-B)

or a tautomer, mesomer, racemate, enantiomer, diastereomer thereof, or a mixture thereof, or a pharmaceutically acceptable salt thereof,
wherein:
$R^1$, $R^2$ and p are as defined in the compound of formula (II).
Further preferably, the MOR agonist or a pharmaceutically acceptable salt thereof is selected from the group consisting of:

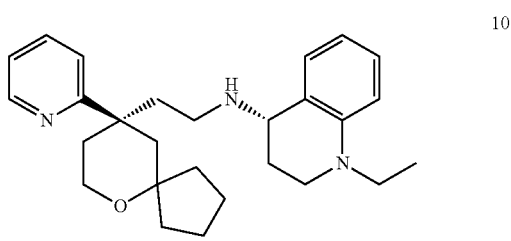

10

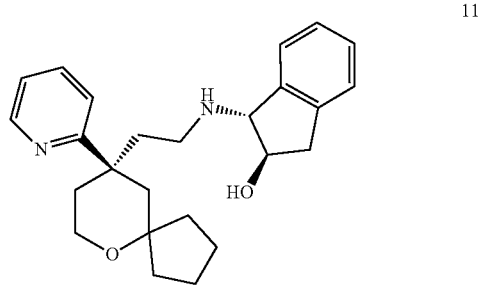

11

-continued
12
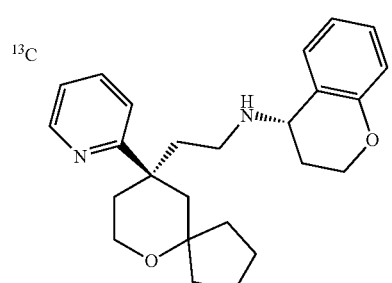
13
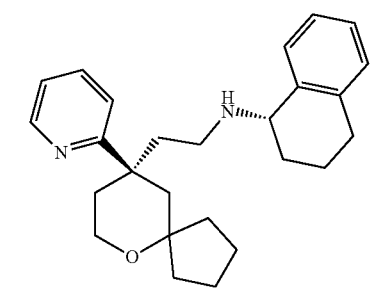
14
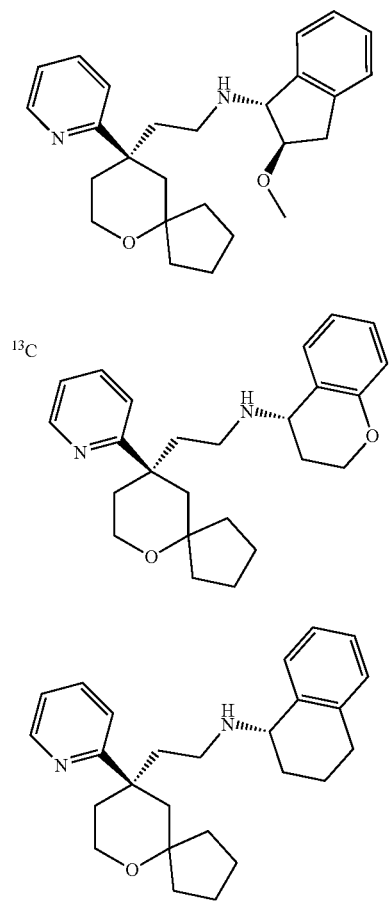
15
16
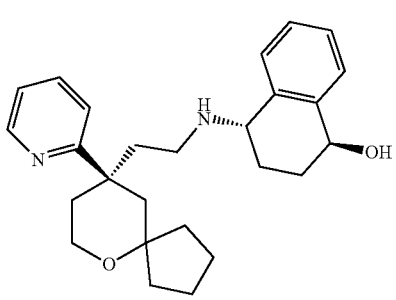
17
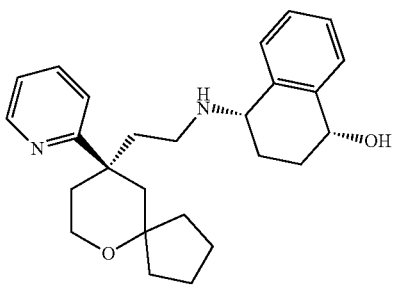
18
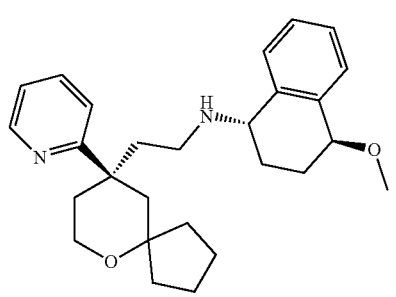
19
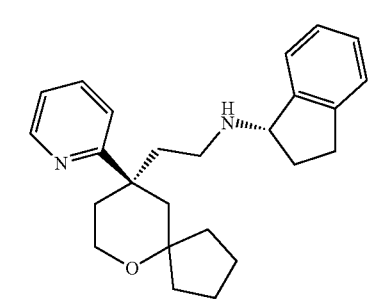
20
21
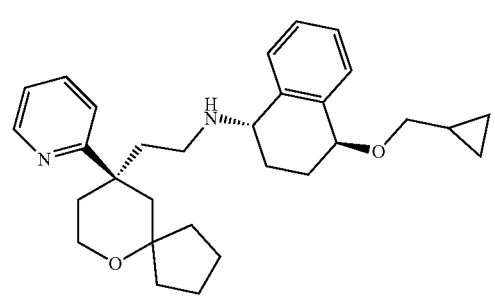

22
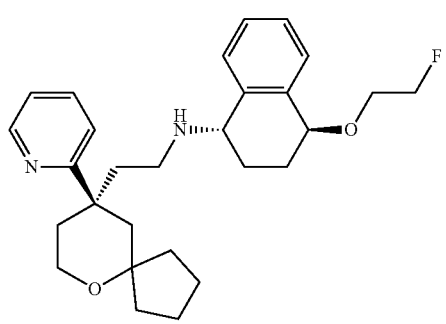
23
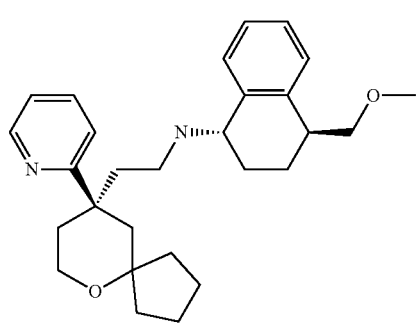
24
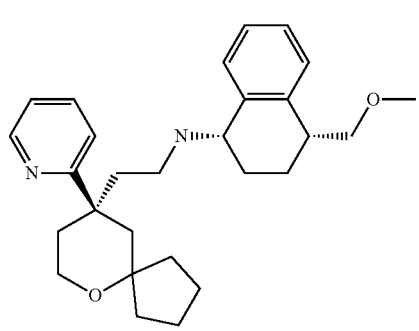
25
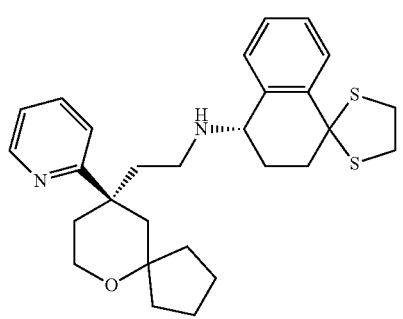
26
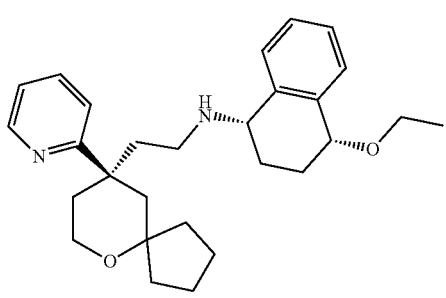
27
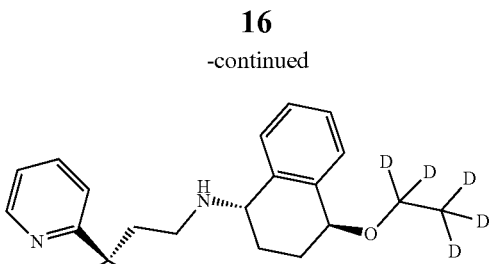
28
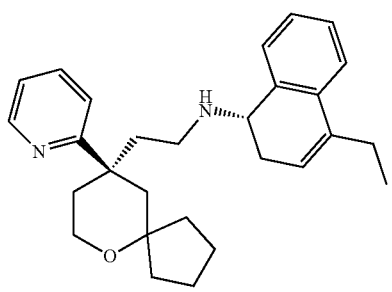
29
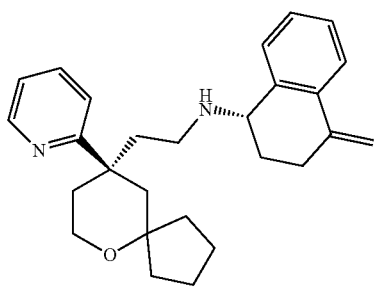
30
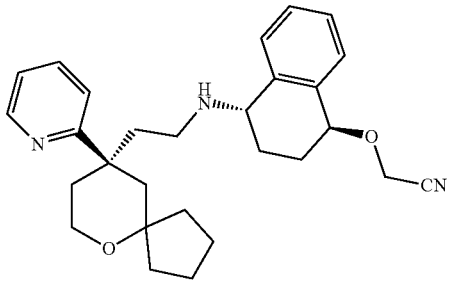
31
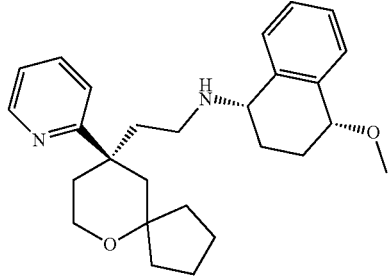

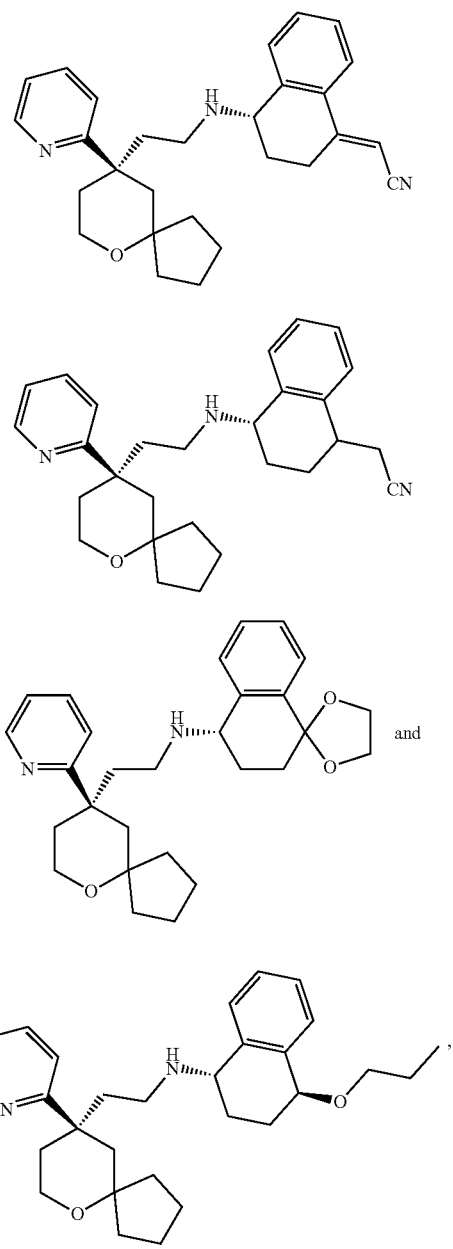

and preferably

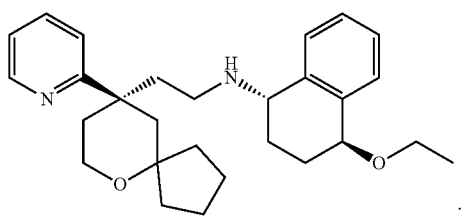

In another preferred embodiment of the present invention, the MOR agonist is selected from the group consisting of dihydromorphone hydrochloride, morphine, oxycodone, buprenorphine, sufentanil, fentanyl, trifentanil, remifentanil, tapentadol, NKTR-181, eluxadoline, benzohydrocodone, loperamide, oliceridine, samidorphan, cebranopadol, tapentadol, methadone, tramadol, TV-46763, hydrocodone, dexketoprofen, oxymorphone, MH-200, levorphanol, Sedatin, desmethyl tramadol, IBCh-07, HS-731, Cyt-1010, trimebutine 3-thiocarbamoyl-benzenesulfonate, thienorphine, trimebutine, TRV-734, TRK-130, hydromorphone, hydromorphone prodrug, EU-178, OREX-1038, AIKO-152, TH-030418, CC-408, XE-440, CYX-6, Org-41793, DPI-125, KN-203, JVA-3025, suboxone, AT-121, VRP-26, endomorphin, NKTR-196, NKTR-174, NKTR-192, NESS-117-OPB, SYK-524, HS-731, HS-198, Dmt-Tic analogue, endorphin 1 derivative, MMP-2200, SEO-16, TLI-0326, BU-08028, BU-08073, TLI-1186, KIN-3031, Neo-1509, GRT-6006, MCP-201, NE-2, MGM-9, EN-3231, NRP-290, NS-7051, CDS-PM-101, frakefamide, BCH-2687, SS-620, VANH-36, 443C81, OHM-329, dermorphin tetrapeptide analogue, sameridine, OHM-3507, SEP-130551, BW-2378W92, sulfazocine, Z-4349, RP-63494, BCH-150, CP-840, and CP-0719.

In the above embodiments, the combination of the KOR agonist and the MOR agonist has a synergistic effect on alleviating and/or treating pain. Preferably, the combination of compound 5 or a pharmaceutically acceptable salt thereof and compound 20 or a pharmaceutically acceptable salt thereof has a synergistic effect on alleviating and/or treating pain.

The present invention provides a method for alleviating and/or treating pain, which comprises administrating to a patient the above KOR agonist salt and MOR agonist.

According to the use of the present invention, the pain is selected from the group consisting of acute pain and chronic pain, and the chronic pain is selected from the group consisting of headache, maxillofacial pain, cervical and occipital pain, neck and shoulder pain, upper limb pain, chest pain, abdominal pain, lumbocrural pain, genital tract pain, urinary tract pain and dysmenorrhea.

According to the use of the present invention, the pain is selected from the group consisting of traumatic pain, inflammatory pain, ischemic pain, pain caused by metabolic diseases, neuropathic pain, pain caused by tissue and organ malformation, labor pain and pain caused by malignant proliferative diseases.

According to the use of the present invention, the traumatic pain is selected from the group consisting of pain caused by surgery (for example postoperative pain caused by appendectomy, open colorectal surgery, hernia repair, prostatectomy, colonectomy, gastrectomy, splenectomy, colectomy, colostomy, pelvic abdominoscopy, tubal ligation, hysterectomy, vasectomy or cholecystectomy), pain after medical treatment (for example pain after colonoscopy, cystoscopy, hysteroscopy, or cervical or endometrial biopsy), fracture pain, burn pain, abdominal traumatic pain, spinal traumatic pain, chest traumatic pain and post-traumatic headache.

According to the use of the present invention, the inflammatory pain is selected from the group consisting of inflammatory headache, tissue inflammatory pain (for example rheumatoid arthritis, rheumatic arthritis, osteoarthritis), organ and gland inflammatory pain (for example gastroesophageal reflux disease, pancreatitis, acute pyelonephritis, ulcerative colitis, cholecystitis, cirrhosis, hepatic cyst, hepatitis, duodenal ulcer or gastric ulcer, esophagitis, gastritis, gastroenteritis, colitis, diverticulitis, intestinal obstruction, ovarian cyst, pelvic inflammatory disease, ulcer perforation, peritonitis, prostatitis, interstitial cystitis) and vascular inflammatory pain.

According to the use of the present invention, the ischemic pain is selected from the group consisting of ischemic headache, limb ischemic pain, tissue ischemic pain, and organ and gland ischemic pain.

According to the use of the present invention, the pain caused by metabolic diseases is selected from the group consisting of pain caused by gout and pain caused by diabetes.

According to the use of the present invention, the neuropathic pain is selected from the group consisting of phantom limb pain, stump pain, burning neuralgia, postherpetic neuralgia, sympathetic-related pain, pain caused by burning foot syndrome, folic acid deficiency peripheral neuralgia, vitamin B12 deficiency peripheral neuralgia, vitamin B1 deficiency multiple neuralgia and leprosy neuralgia.

According to the use of the present invention, the pain caused by malignant proliferative diseases is pain caused by tumors, including but not limited to pain caused by leukemia, lymphoma, myeloma, breast cancer, lung cancer, esophageal cancer, stomach cancer, colorectal cancer, liver cancer, pancreatic cancer, head and neck cancer, kidney cancer, bladder cancer, prostate cancer, ovarian cancer, endometrial cancer, cervical cancer, osteosarcoma, soft tissue sarcoma, melanoma, and brain tumor.

According to the use of the present invention, the pain is a moderate to severe pain. Preferably, the moderate to severe pain is selected from the group consisting of traumatic pain, labor pain, pain caused by tumors and inflammatory pain.

According to the use of the present invention, the moderate to severe pain is not applicable and/or not sensitive to non-opioid analgesics or weak opioid analgesics.

The present invention provides a combination of the above KOR agonist and the above MOR agonist for use as a medicament for alleviating and/or treating pain.

According to the use of the present invention, the weight ratio of the KOR agonist to the MOR agonist is 0.01-1000, or selected from the group consisting of 1000/1, 750/1, 500/1, 400/1, 250/1, 200/1, 100/1, 100/3, 90/1, 80/1, 75/1, 70/1, 60/1, 50/1, 40/1, 30/1, 30/7, 20/1, 20/7, 20/3, 20/9, 25/1, 25/2, 25/3, 25/4, 25/6, 25/7, 25/8, 25/9, 25/18, 15/1, 15/2, 15/4, 18/1, 18/5, 18/7, 14/1, 14/3, 14/5, 14/9, 12/1, 12/5, 12/7, 10/1, 10/3, 10/7, 10/9, 9/1, 9/2, 9/4, 8/1, 8/3, 8/5, 7/1, 7/2, 7/3, 7/4, 7/5, 7/6, 6/1, 6/5, 5/1, 5/2, 5/3, 5/4, 4/1, 4/3, 3/1, 3/2, 2/1, 1/1, 1/2, 1/3, 1/5, 1/10, 1/20, 1/25, 1/30 and 1/50, and preferably 1/1, 5/3, 2/1, 15/7, 5/2, 3/1, 10/3, 15/4, 4/1, 9/2, 5/1, 6/1, 25/4, 20/3, 15/2, 8/1, 9/1, 10/1, 12/1, 25/2, 15/1, 20/1, 25/1, 30/1, 40/1, 50/1, 60/1, 70/1, 75/1, 80/1, 90/1, 100/3, 100/1, 200/1 or 250/1.

According to the use of the present invention, the administration dose of the KOR agonist is 0.001-250 mg, and preferably 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.05 mg, 0.15 mg, 0.2 mg, 0.25 mg, 0.3 mg, 0.4 mg, 0.5 mg, 0.6 mg, 0.75 mg, 0.8 mg, 0.9 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.5 mg, 5 mg, 6 mg, 7 mg, 7.5 mg, 8 mg, 9 mg, 10 mg, 12.5 mg, 15 mg, 17.5 mg, 18 mg, 20 mg, 25 mg, 30 mg, 40 mg, 50 mg, 75 mg, 100 mg, 125 mg, 150 mg, 175 mg, 200 mg, or 250 mg; the administration dose of the MOR agonist is 0.001-50 mg, and preferably 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.025 mg, 0.03 mg, 0.04 mg, 0.05 mg, 0.06 mg, 0.07 mg, 0.075 mg, 0.15 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.2 mg, 1.25 mg, 1.5 mg, 1.75 mg, 2 mg, 2.2 mg, 2.25 mg, 2.5 mg, 2.75 mg, 3 mg, 3.25 mg, 3.5 mg, 3.75 mg, 4 mg, 4.5 mg, 5 mg, 6 mg, 7 mg, 7.5 mg, 8 mg, 9 mg, 10 mg, 12.5 mg, 15 mg, 17.5 mg, 20 mg, 25 mg, 30 mg, 40 mg, or 50 mg.

According to the use of the present invention, further preferably, the KOR agonist is compound 5 or a pharmaceutically acceptable salt thereof, the administration dose is 0.001-20 mg, and preferably 0.005 mg, 0.01 mg, 0.03 mg, 0.05 mg, 0.1 mg, 0.15 mg, 0.2 mg, 0.25 mg, 0.3 mg, 0.4 mg, 0.5 mg, 0.6 mg, 0.75 mg, 0.8 mg, 0.9 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.5 mg, 5 mg, 6 mg, 7 mg, 7.5 mg, 8 mg, 9 mg, 10 mg, 12.5 mg, 15 mg, 17.5 mg, 18 mg, or 20 mg.

According to the use of the present invention, further preferably, the MOR agonist is compound 20 or a pharmaceutically acceptable salt thereof, the administration dose is 0.001-20 mg, and preferably 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.025 mg, 0.03 mg, 0.04 mg, 0.05 mg, 0.06 mg, 0.07 mg, 0.075 mg, 0.15 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.2 mg, 1.25 mg, 1.5 mg, 1.75 mg, 2 mg, 2.2 mg, 2.25 mg, 2.5 mg, 2.75 mg, 3 mg, 3.25 mg, 3.5 mg, 3.75 mg, 4 mg, 4.5 mg, 5 mg, 6 mg, 7 mg, 7.5 mg, 8 mg, 9 mg, 10 mg, 12.5 mg, 15 mg, 17.5 mg, or 20 mg.

According to the use of the present invention, the administration dose of the KOR agonist is 0.01-500 µg/kg, and preferably 0.01 µg/kg, 0.05 µg/kg, 0.1 µg/kg, 0.2 µg/kg, 0.25 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 2 µg/kg, 2.5 µg/kg, 3 µg/kg, 4 µg/kg, 5 µg/kg, 8 µg/kg, 10 µg/kg, 15 µg/kg, 20 µg/kg, 24 µg/kg, 25 µg/kg, 30 µg/kg, 40 µg/kg, 50 µg/kg, 60 µg/kg, 70 µg/kg, 75 µg/kg, 80 µg/kg, 90 µg/kg, 100 µg/kg, 200 µg/kg, 250 µg/kg, 300 µg/kg, 400 µg/kg, or 500 µg/kg; the administration dose of the MOR agonist is 0.001-500 µg/kg, and preferably 0.003 µg/kg, 0.005 µg/kg, 0.01 µg/kg, 0.05 µg/kg, 0.1 µg/kg, 0.2 µg/kg, 0.25 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 2 µg/kg, 2.5 µg/kg, 3 µg/kg, 4 µg/kg, 5 µg/kg, 8 µg/kg, 10 µg/kg, 15 µg/kg, 20 µg/kg, 24 µg/kg, 25 µg/kg, 30 µg/kg, 40 µg/kg, 50 µg/kg, 60 µg/kg, 70 µg/kg, 75 µg/kg, 80 µg/kg, 90 µg/kg, 100 µg/kg, 200 µg/kg, 250 µg/kg, 300 µg/kg, 400 µg/kg, or 500 µg/kg.

According to the use of the present invention, the KOR agonist is compound 5 or a pharmaceutically acceptable salt thereof, the administration dose is 0.01-150 µg/kg, and preferably 0.01 µg/kg, 0.05 µg/kg, 0.1 µg/kg, 0.2 µg/kg, 0.25 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 2 µg/kg, 2.5 µg/kg, 3 µg/kg, 4 µg/kg, 5 µg/kg, 8 µg/kg, 10 µg/kg, 15 µg/kg, 20 µg/kg, 24 µg/kg, 25 µg/kg, 40 µg/kg, 50 µg/kg, 75 µg/kg, or 100 µg/kg.

According to the use of the present invention, the MOR agonist is compound 20 or a pharmaceutically acceptable salt thereof, the administration dose is 0.001-150 µg/kg, and preferably 0.003 µg/kg, 0.005 µg/kg, 0.01 µg/kg, 0.05 µg/kg, 0.1 µg/kg, 0.2 µg/kg, 0.25 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 2 µg/kg, 2.5 µg/kg, 3 µg/kg, 4 µg/kg, 5 µg/kg, 8 µg/kg, 10 µg/kg, 15 µg/kg, 20 µg/kg, 24 µg/kg, 25 µg/kg, 30 µg/kg, 40 µg/kg, 50 µg/kg, 60 µg/kg, 70 µg/kg, 75 µg/kg, 80 µg/kg, 90 µg/kg, or 100 µg/kg.

The administration mode of the combination of the present invention is selected from the group consisting of: simultaneous administration, co-administration after separate formulation, and sequential administration after separate formulation.

The present invention further relates to a use of a combination of a MOR agonist and a KOR agonist in the preparation of a medicament for alleviating and/or treating pain, wherein the initial administration dose of the KOR agonist is 0.05-50 times of the maintenance dose, and the initial administration dose of the MOR agonist is 1-50 times of the maintenance dose.

The present invention further relates to a use of a combination of a KOR agonist and a MOR agonist in the preparation of a medicament for alleviating and/or treating pain, wherein the administration frequency of the KOR agonist is once a day, twice a day, three times a day, once a week, once every two weeks, once every three weeks, once a month, and the administration frequency of the MOR agonist is once a day, twice a day, three times a day, once a week, once every two weeks, once every three weeks, or once a month.

In the above embodiments, the combination also optionally comprises a third component selected from the group consisting of an opioid, glucocorticoid, non-steroidal anti-inflammatory drug, local anesthetic, anti-depressant, calcium channel antagonist, anti-convulsant, adrenal beta receptor blocker, anesthetic, and anesthesia inducer.

The present invention also relates to a pharmaceutical composition of a KOR agonist and a MOR agonist optionally comprising one or more pharmaceutically acceptable carriers, excipients and/or diluents. The pharmaceutical composition can be formulated into any one of the pharmaceutically acceptable dosage forms. For example, a pharmaceutical formulation comprising a KOR agonist and a MOR agonist as the active ingredients can be formulated into a tablet, capsule, pill, granule, solution, suspension, syrup, injection (including injection solution, sterile powder for injection and concentrated solution for injection), suppository, inhalant or spray.

The pharmaceutical composition of the KOR agonist and the MOR agonist of the present invention can be administrated alone, or in combination with one or more therapeutic agents.

In the use of a KOR agonist and a MOR agonist in the preparation of a medicament for alleviating and/or treating pain according to the present invention, the KOR agonist and the MOR agonist can be administrated orally or parenterally (including, but not limited to subcutaneous injection, intravenous injection and intraperitoneal injection).

The components to be combined (for example, the KOR agonist and the MOR agonist, the KOR agonist and the MOR agonist and the optional third component) can be administrated simultaneously or sequentially separately. Moreover, the components to be combined can also be co-administrated in the same formulation or separately in different formulations.

In the present invention, the term "combined administration" or "co-administration" is an administration mode, including various situations in which the two or more drugs are administrated sequentially or simultaneously. The term "simultaneously" herein means that the KOR agonist and the MOR agonist, or the KOR agonist and the MOR agonist and the optional third component are administered during the same administration cycle, for example, the two or more drugs are administrated within one day, three days, one week, two weeks or one month. The term "sequential or successive" administration includes situations in which the KOR agonist and the MOR agonist, or the KOR agonist and the MOR agonist and the optional third component are administrated respectively, in different administration cycles. These administration modes all belong to the combined administration of the present invention.

The term "effective amount" according to the present invention encompasses an amount sufficient to ameliorate or prevent a symptom or sign of a medical condition. The term "effective amount" also refers to an amount sufficient to allow or facilitate diagnosis. An effective amount for a particular patient or veterinary subject may vary, depending on factors such as the condition to be treated, the general health of the patient, the route and dose of administration, and the severity of side effects. An effective amount can be the maximal dose or administration regimen that avoids significant side effects or toxic effects.

DEFINITIONS

In the specification and claims of the present application, unless otherwise indicated, the scientific and technical terms used herein have the meanings generally understood by a person skilled in the art. However, in order to understand the present invention better, definitions and explanations of some related terms are provided. In addition, when the definitions and explanations of the terms provided in the present application are inconsistent with the meanings generally understood by a person skilled in the art, the definitions and explanations of the terms provided in the present application shall prevail.

The term "hydroxyalkyl" refers to an alkyl group substituted by hydroxy(s), wherein the alkyl is as defined below.

The term "haloalkyl" refers to an alkyl group substituted by one or more halogens, wherein the alkyl is as defined below.

The term "hydroxy" refers to an —OH group.

The term "halogen" refers to fluorine, chlorine, bromine or iodine.

The term "amino" refers to a —$NH_2$ group.

The term "cyano" refers to a —CN group.

The term "nitro" refers to a —$NO_2$ group.

The term "carboxy" refers to a —C(O)OH group.

The term "alkoxycarbonyl" refers to a —C(O)O(alkyl) or —C(O)O(cycloalkyl) group, wherein the alkyl and cycloalkyl are as defined below.

All of "X is selected from the group consisting of A, B, or C", "X is selected from the group consisting of A, B and C", "X is A, B or C", "X is A, B and C" and the like, are of the same meaning, i.e., X can be any one or more of A, B, and C.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, carboxy and alkoxycarbonyl.

The term "cycloalkyl" refers to a saturated or partially unsaturated monocyclic or polycyclic hydrocarbon substituent group having 3 to 20 carbon atoms, preferably 3 to 12 carbon atoms, more preferably 3 to 6 carbon atoms, and most preferably 5 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

The term "spiro cycloalkyl" refers to a 5 to 20 membered polycyclic group with individual rings connected through one shared carbon atom (called a spiro atom), wherein the rings can contain one or more double bonds, but none of the rings has a completely conjugated π-electron system. The spiro cycloalkyl is preferably 6 to 14 membered spiro cycloalkyl, and more preferably 7 to 10 membered spiro cycloalkyl. According to the number of the spiro atoms shared between the rings, the spiro cycloalkyl can be divided into mono-spiro cycloalkyl, di-spiro cycloalkyl, or poly-spiro cycloalkyl, and the spiro cycloalkyl is preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

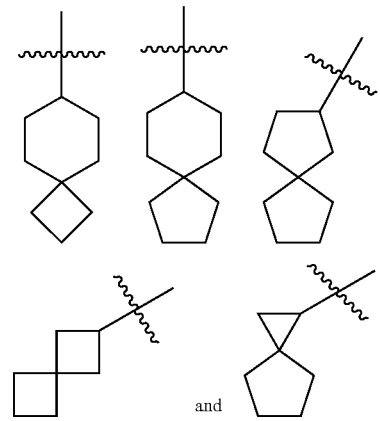

and

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated π-electron system. The fused cycloalkyl is preferably 6 to 14 membered fused cycloalkyl, and more preferably 7 to 10 membered fused cycloalkyl. According to the number of membered rings, the fused cycloalkyl can be divided into bicyclic, tricyclic, tetracyclic or polycyclic fused cycloalkyl, and the fused cycloalkyl is preferably bicyclic or tricyclic fused cycloalkyl, and more preferably 5-membered/5-membered, or 5-membered/6-membered bicyclic fused cycloalkyl. Non-limiting examples of fused cycloalkyl include:

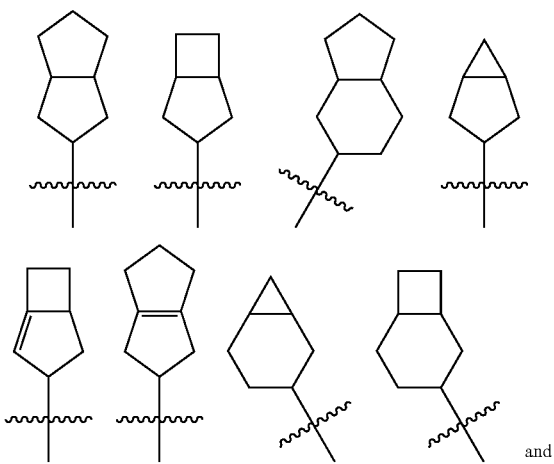

and

-continued

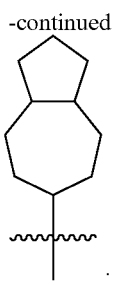

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated π-electron system. The bridged cycloalkyl is preferably 6 to 14 membered bridged cycloalkyl, and more preferably 7 to 10 membered bridged cycloalkyl. According to the number of membered rings, the bridged cycloalkyl can be divided into bicyclic, tricyclic, tetracyclic or polycyclic bridged cycloalkyl, and the bridged cycloalkyl is preferably bicyclic, tricyclic or tetracyclic bridged cycloalkyl, and more preferably bicyclic or tricyclic bridged cycloalkyl. Non-limiting examples of bridged cycloalkyls include:

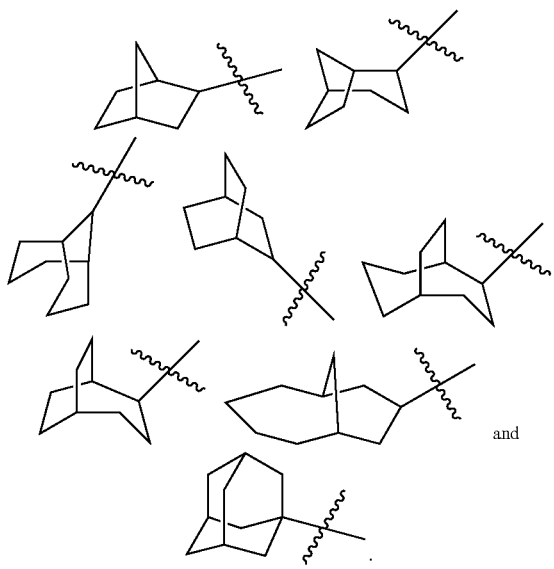

The ring of cycloalkyl can be fused to the ring of aryl, heteroaryl or heterocyclyl, wherein the ring bound to the parent structure is cycloalkyl. Non-limiting examples include indanyl, tetrahydronaphthyl, benzocycloheptyl and the like, and preferably benzocyclopentyl, tetrahydronaphthyl. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon group, wherein one or more ring atoms are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, the heterocyclyl has 3 to 8 ring atoms wherein 1 to 3 atoms are heteroatoms; and most preferably 5 to 6 ring atoms wherein 1 to 2 or 1 to 3 atoms are heteroatoms. Non-limiting examples of monocyclic heterocyclyl include pyrrolidinyl, imidazolidinyl, tetrahydrofuranyl, tetrahydropyranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl and the like, and preferably tetrahydropyranyl, piperidinyl, pyrrolidinyl. Polycyclic heterocyclyl includes a heterocyclyl having a spiro ring, fused ring or bridged ring.

The term "spiro heterocyclyl" refers to a 5 to 20 membered polycyclic heterocyclyl group with individual rings connected through one shared atom (called a spiro atom), wherein one or more ring atoms are heteroatoms selected from the group consisting of N, O and $S(O)_m$ (wherein m is an integer of 0 to 2), with the remaining ring atoms being carbon atoms, where the rings can contain one or more double bonds, but none of the rings has a completely conjugated π-electron system. The spiro heterocyclyl is preferably 6 to 14 membered spiro heterocyclyl, and more preferably 7 to 10 membered spiro heterocyclyl. According to the number of the spiro atoms shared between the rings, the spiro heterocyclyl can be divided into mono-spiro heterocyclyl, di-spiro heterocyclyl, or poly-spiro heterocyclyl, and the spiro heterocyclyl is preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

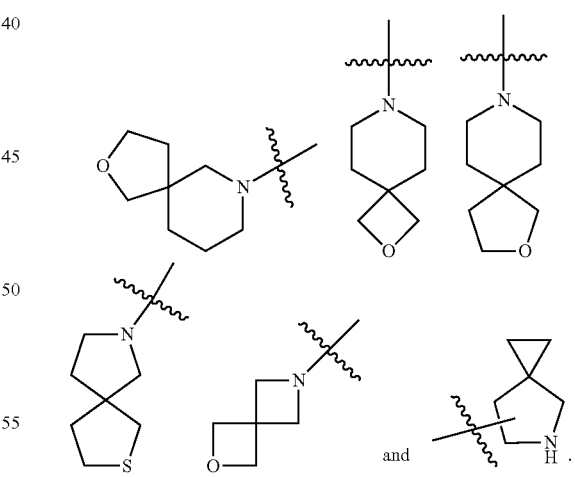

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O and $S(O)_m$ (wherein m is an integer of 0 to 2), with the remaining ring atoms being carbon atoms. The fused heterocyclyl is preferably 6 to 14 membered fused heterocyclyl, and more preferably 7 to 10 membered fused heterocyclyl. According to the number of membered rings, the fused heterocyclyl can be divided into bicyclic, tricyclic, tetracyclic or polycyclic fused heterocyclyl, and the fused heterocyclyl is preferably bicyclic or tricyclic fused heterocyclyl, and more preferably 5-membered/5-membered or 5-membered/6-membered bicyclic fused heterocyclyl. Non-limiting examples of fused heterocyclyl include:

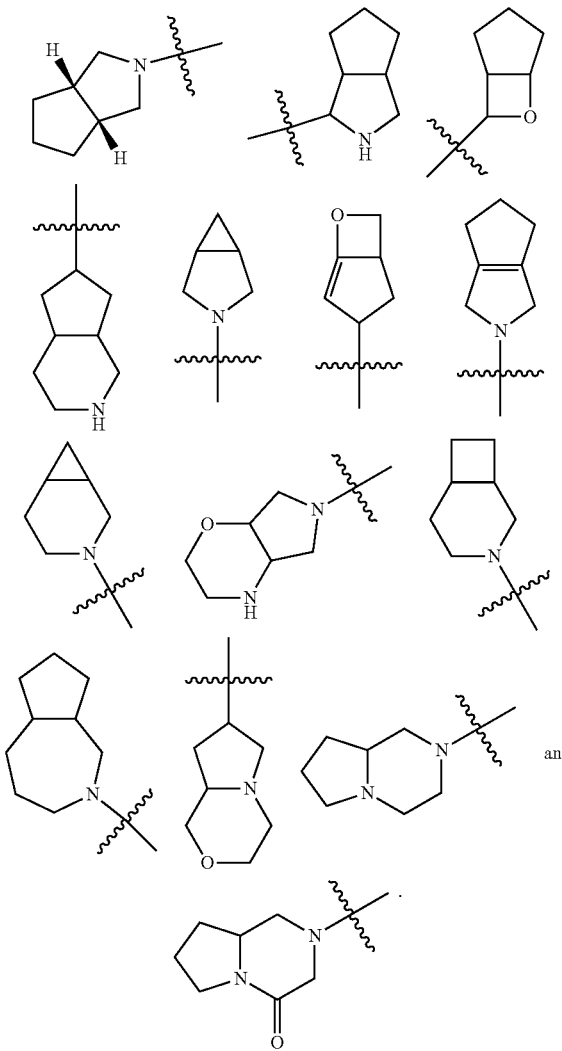

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O and S(O)$_m$ (wherein m is an integer of 0 to 2), with the remaining ring atoms being carbon atoms. The bridged heterocyclyl is preferably 6 to 14 membered bridged heterocyclyl, and more preferably 7 to 10 membered bridged heterocyclyl. According to the number of membered rings, the bridged heterocyclyl can be divided into bicyclic, tricyclic, tetracyclic or polycyclic bridged heterocyclyl, and the bridged heterocyclyl is preferably bicyclic, tricyclic or tetracyclic bridged heterocyclyl, and more preferably bicyclic or tricyclic bridged heterocyclyl. Non-limiting examples of bridged heterocyclyls include:

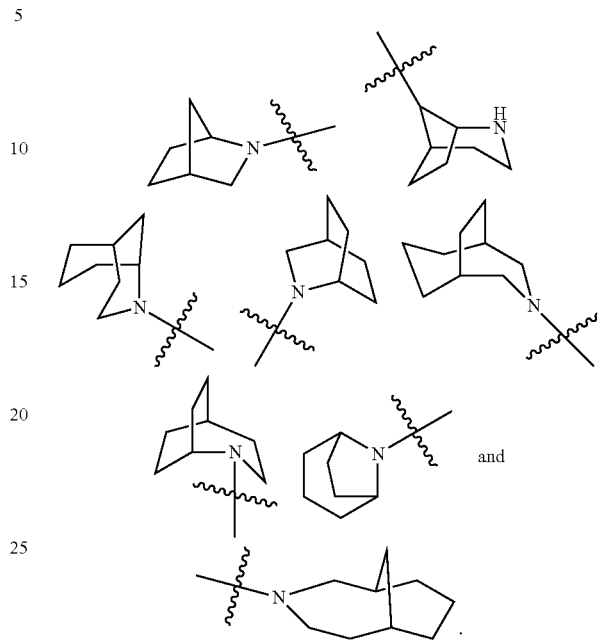

The ring of heterocyclyl can be fused to the ring of aryl, heteroaryl or cycloalkyl, wherein the ring bound to the parent structure is heterocyclyl. Non-limiting examples thereof include:

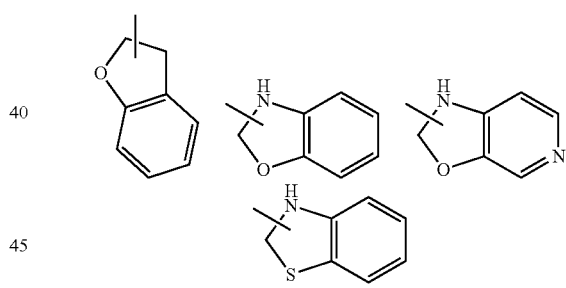

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, carboxy and alkoxycarbonyl.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 10 membered aryl, and more preferably 5 to 6 membered aryl, for example, phenyl and naphthyl. The ring of aryl can be fused to the ring of heteroaryl, heterocyclyl or cycloalkyl, wherein the ring bound to the parent structure is aryl ring. Non-limiting examples thereof include:

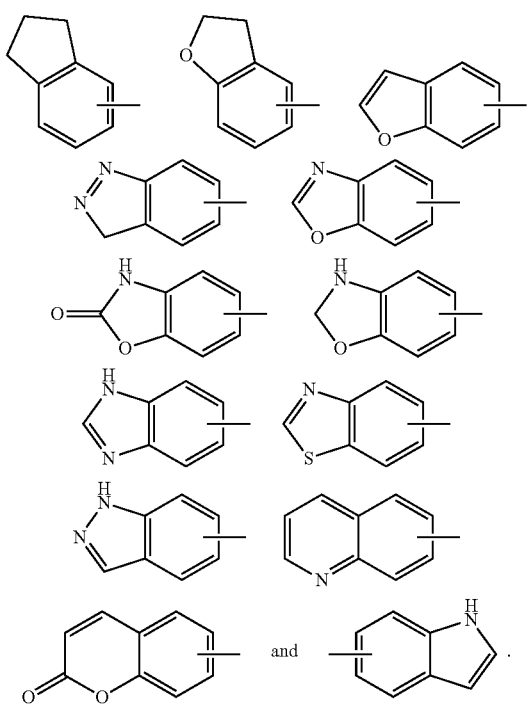

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, carboxy and alkoxycarbonyl.

The term "heteroaryl" refers to a 5 to 14 membered heteroaromatic system having 1 to 4 heteroatoms selected from the group consisting of O, S and N. The heteroaryl is preferably 5 to 10 membered heteroaryl having 1 to 3 heteroatoms, more preferably 5 or 6 membered heteroaryl having 1 to 2 heteroatoms, preferably for example, imidazolyl, furyl, thienyl, thiazolyl, pyrazolyl, oxazolyl, pyrrolyl, tetrazolyl, pyridyl, pyrimidinyl, thiadiazolyl, pyrazinyl and the like, preferably imidazolyl, pyrazolyl, pyrimidinyl, thiazolyl, and more preferably pyrazolyl. The ring of heteroaryl can be fused to the ring of aryl, heterocyclyl or cycloalkyl, wherein the ring bound to the parent structure is heteroaryl ring. Non-limiting examples thereof include:

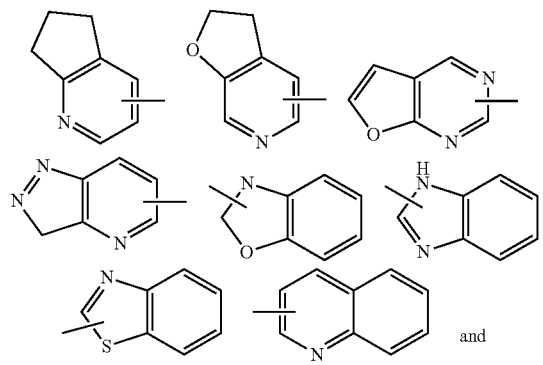

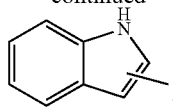

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, carboxy and alkoxycarbonyl.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, carboxy and alkoxycarbonyl.

The term "amino protecting group" refers to a group suitable for protecting (preventing) an amino group from a chemical reaction, and it is easily removed after completion of a chemical reaction at other parts of the molecule. Typical representatives of these groups include unsubstituted or substituted acyl, unsubstituted or substituted allyl, aryl, arylalkoxymethyl, arylalkyl, or heterocyclyl formed together with a nitrogen atom and salt. Non-limiting examples of amino protecting group include tert-butoxycarbonyl (Boc), benzyloxycarbonyl, isobutoxycarbonyl, fluorenylmethoxycarbonyl (Fmoc), benzoyl, substituted benzoyl, butyryl, acetyl, trifluoroacetyl, phthaloyl (Pht), succinimidyl, maleimido, benzyl, allyloxycarbonyl, p-methoxybenzyl and the like. These groups can be optionally substituted by one or more substituents selected from the group consisting of halogen, alkyl, alkoxy, hydroxy, nitro, acylamino, benzyl substituted by acyl and the like, o-methylbenzyl, trityl and diphenylmethyl. The amino protecting group is preferably tert-butoxycarbonyl and fluorenylmethoxycarbonyl (Fmoc).

The term "synergistic effect" includes additive effect, potentiating effect, and sensitizing effect. The "synergistic effect" of the present invention includes but is not limited to reducing the tolerance when the KOR agonist or the MOR agonist is used alone, reducing the dose when the KOR agonist or the MOR agonist is used alone, reducing the side effects when the KOR agonist or the MOR agonist is used alone, improving the effect of alleviating and/or treating pain when the same dose of the KOR agonist and/or the same dose of the MOR agonist is used alone.

The term "acute pain" refers to a pain caused by harmful irritation resulting from injury and/or disease of skin, deep body structures or organs, or a short-term pain caused by abnormal function of muscles or organs that do not produce actual tissue injury.

The term "chronic pain" refers to a pain that continues beyond the usual course of an acute disease or a reasonable time for injury healing, a pain associated with the chronic pathological process that causes persistent pain, or a pain that recurs at a certain interval (several days, weeks, months and years). Moreover, chronic pain also includes a pain that still exists after the cure should have been reached or after the usual course of treatment.

The term "inflammatory pain" refers to a pain caused by nerve stimulation of local acute inflammation or chronic inflammation.

The term "ischemic pain" refers to a pain caused by poor blood supply to the limbs or organs.

The term "neuropathic pain" refers to a pain caused by primary or secondary injury or dysfunction or transient disturbance of the peripheral or central nervous system.

The term "pain caused by malignant proliferative diseases" refers to a pain caused by tumors and cancers resulting from the malignant proliferation of somatic cells, a pain caused by lesions resulting from the malignant proliferation of virus in human organs, glands, blood system and skin, and a pain caused by lesions resulting from the malignant proliferation of bacteria in human organs, glands, blood system and skin.

The term "tissue" refers to a population of cells that are identical or similar in morphology and identical in function, including but not limited to epithelial tissue, connective tissue, muscle tissue, and neural tissue, for example cartilage tissue, bone tissue, skeletal muscle, myocardium, and smooth muscle.

The term "moderate to severe pain" refers to a severe pain that can only be alleviated by analgesic, a pain that affects disease treatment and/or vital signs, and a persistent pain that affects recovery.

The term "initial dose" refers to a dose administrated for the first time for eliminating clinical symptoms when a continuous administration is required.

The term "maintenance dose" refers to a dose administrated for consolidating and maintaining the efficacy after the clinical symptoms are controlled or alleviated.

The term "administration according to the need for pain" refers to an administration for the purpose of alleviating and/or treating pain according to the degree of mammalian self-perception of pain.

The meaning of the term "surgery" is not limited to the conventional definition of surgery that includes the content disclosed in the surgery classification catalogue (2011 edition) of Ministry of Health. The surgery of the present invention broadly encompasses surgical procedures that have at least one incision in the skin and mucosa, and non-conventionally defined medical procedures (for example, interventional procedures involving diagnosis and treatment).

The term "pain caused by surgery" refers to a pain response after the injury or stimulation of the surgery on the body's tissue, encompassing preoperative, intraoperative and postoperative pain during perioperative period, including but not limited to pain after surgical procedures (for example postoperative pain caused by appendectomy, open colorectal surgery, hernia repair, prostatectomy, colonectomy, gastrectomy, splenectomy, colectomy, colostomy, pelvic abdominoscopy, tubal ligation, hysterectomy, vasectomy or cholecystectomy), pain after medical treatment (for example pain after colonoscopy, cystoscopy, hysteroscopy, or cervical or endometrial biopsy).

The term "pain caused by tumors" refers to a pain directly caused by tumors, a pain caused by the treatment of tumors, a pain indirectly caused by tumors.

DESCRIPTION OF THE DRAWINGS

FIG. 1 shows the effect of the combination of the KOR agonist and the MOR agonist (compound 5 and compound 20) of the present invention on the mechanical withdrawal threshold of rats in the incision pain test.

DETAILED DESCRIPTION OF THE INVENTION

The exemplary experimental solutions for the use of the composition of the present invention in alleviating and/or treating pain are provided below in order to demonstrate the favorable activity and beneficial technical effects of the composition of the present invention. However, it should be understood that the following experimental solutions are merely examples of the present invention and are not intended to limit the scope of the present invention. A person skilled in the art, based on the teachings of the specification, can make suitable modifications or alterations to the technical solutions of the present invention without departing from the spirit and scope of the present invention.

Example 1. Preparation of Compound 5

Compound 5 was identified by nuclear magnetic resonance (NMR) and/or mass spectrometry (MS). NMR shifts ($\delta$) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for column chromatography.

Prep Star SD-1 (Varian Instruments Inc.) or SFC-multigram (Berger Instruments Inc.) is used for chiral preparative column chromatography.

The known starting materials of the present invention can be prepared by the known methods in the art, or can be purchased from ABCR GmbH & Co. KG, Acros Organnics, Aldrich Chemical Company, Accela ChemBio Inc., or Dari Chemical Company, etc.

Unless otherwise stated, the solution refers to an aqueous solution.

Unless otherwise stated, the reaction temperature is room temperature from 20° C. to 30° C.

The reaction process in the examples was monitored by thin layer chromatography (TLC), and the developing solvent system used in the reactions included: A: dichloromethane and methanol system, B: n-hexane and ethyl acetate system, C: petroleum ether and ethyl acetate system, D: acetone. The volume ratio of the solvents was adjusted according to the polarity of the compounds. The eluent system in column chromatography and the developing solvent system in thin layer chromatography for purification of the compounds included: A: dichloromethane and methanol system, B: n-hexane and ethyl acetate system, C: dichloromethane and acetone system. The volume ratio of the solvents was adjusted according to the polarity of the compounds, and a small quantity of alkaline reagent such as triethylamine or acidic reagent such as acetic acid can also be added for adjustment.

High pressure liquid chromatograph used in the high performance liquid chromatography in the examples was a Gilson-281, the chromatographic column was a Shim-pack PREP-ODS from Shimadzu, the mobile phase used was a trifluoroacetic acid buffer system, i.e., water (containing 0.05% trifluoroacetate)-acetonitrile.

Each of the compounds in the form of a trifluoroacetate salt in the examples can be obtained in a free state by the following general method: the trifluoroacetate salt thereof was dissolved in a suitable solvent (such as methanol, ethanol, tetrahydrofuran, acetone, etc.), and a weak base was added (such as sodium bicarbonate, sodium carbonate, potassium carbonate, etc.) to adjust the pH to be neutral, the solution was concentrated under reduced pressure, and the residue was purified to obtain a free state

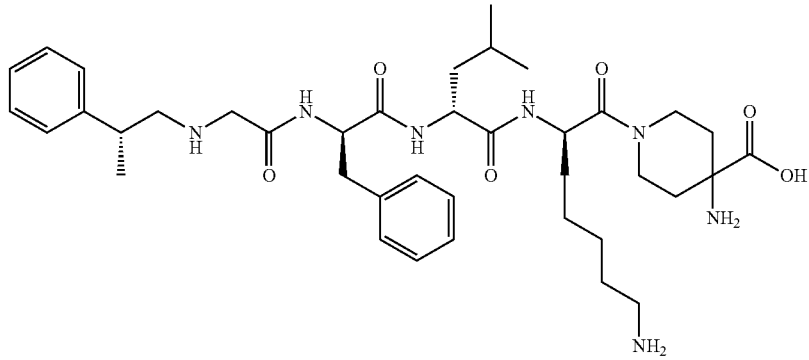

5

4-Amino-1-((2R,5R,8R,14R)-2-(4-aminobutyl)-8-benzyl-5-isobutyl-4,7,10-trioxo-14-phenyl-3,6,9,12-tetraazapentadecan-1-oyl)piperidine-4-carboxylic acid

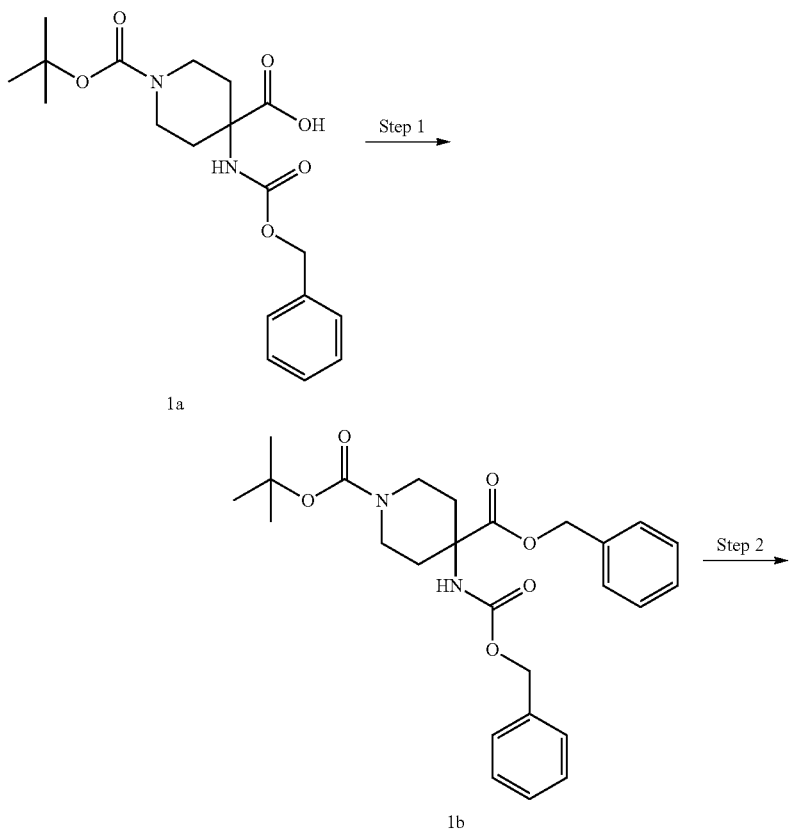

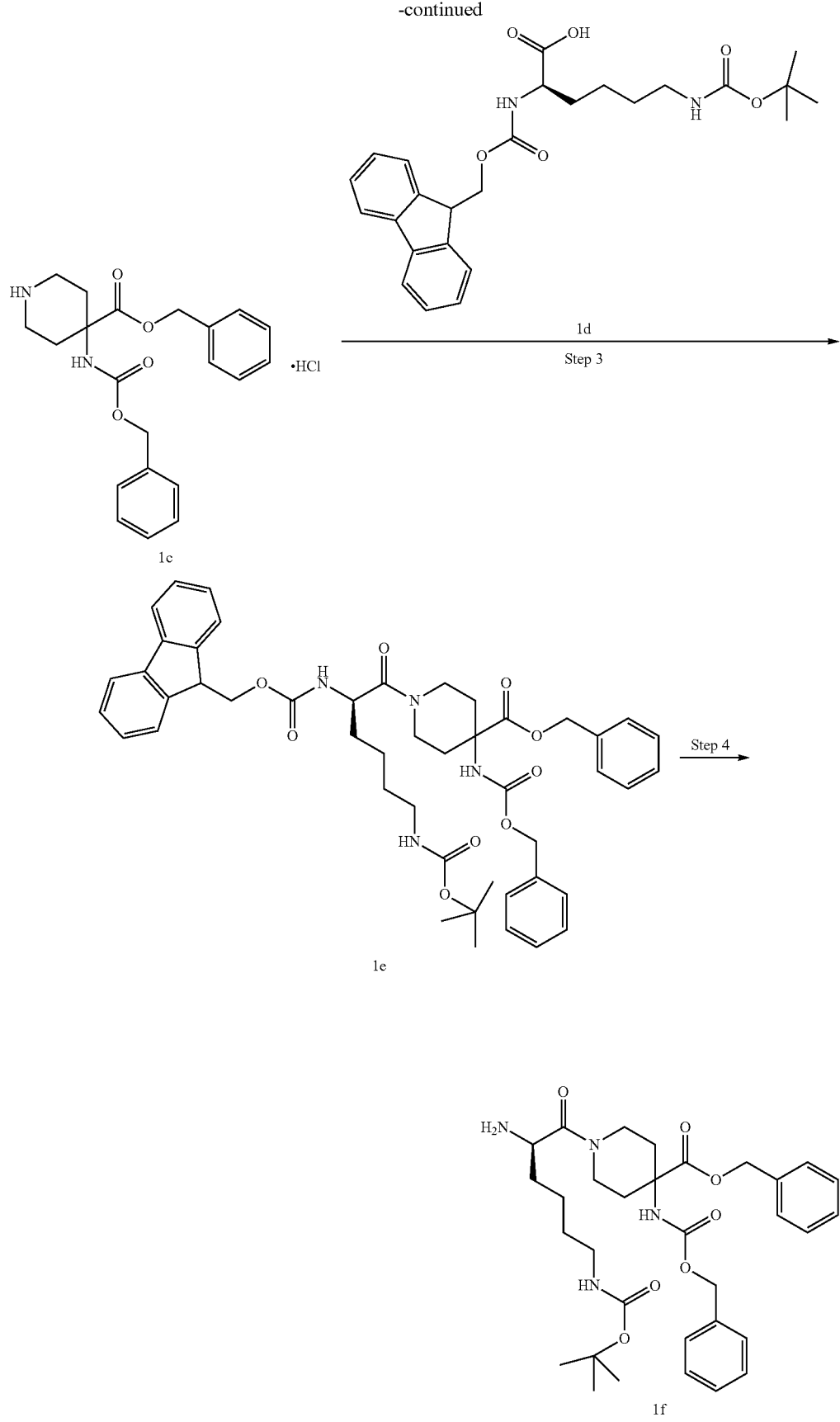

-continued
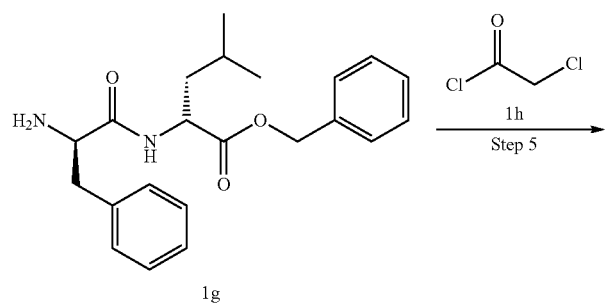
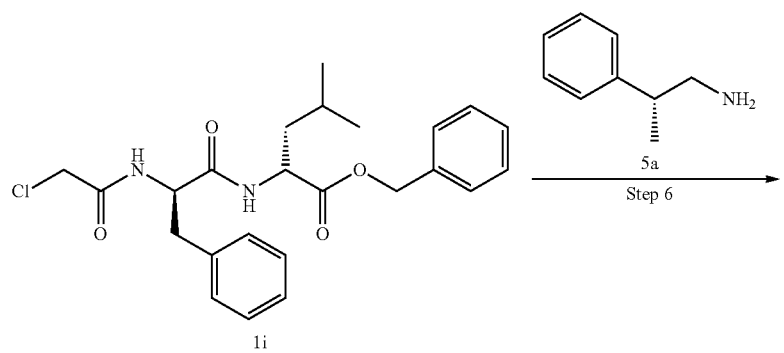
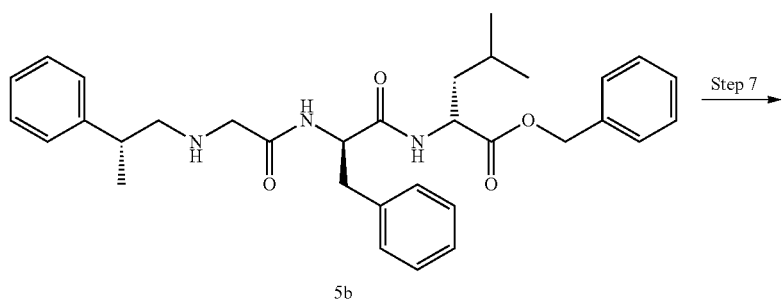
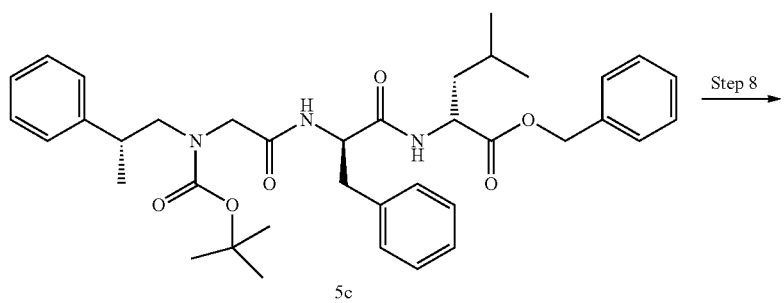

-continued
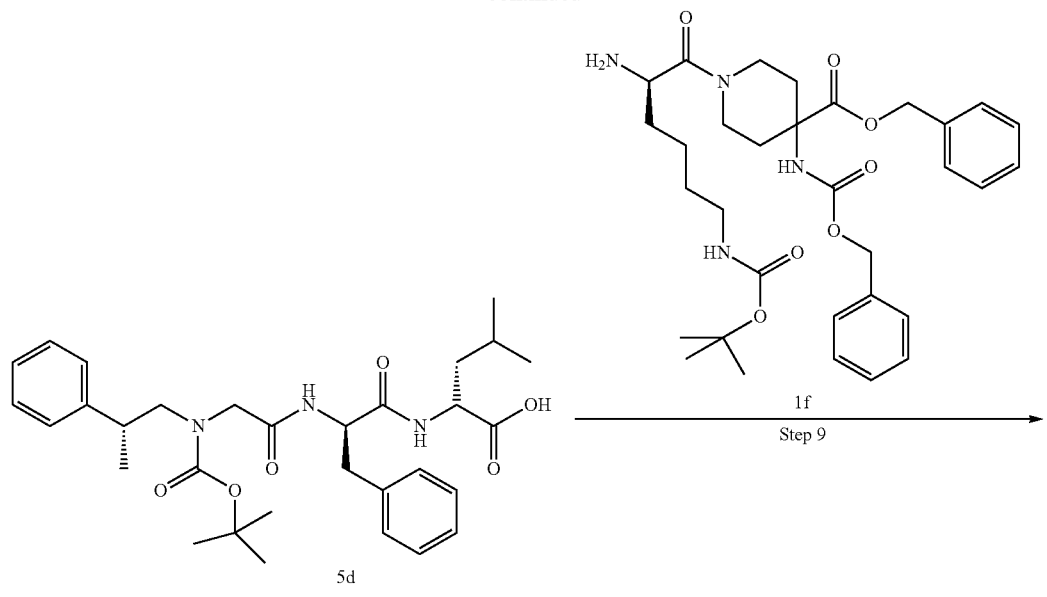
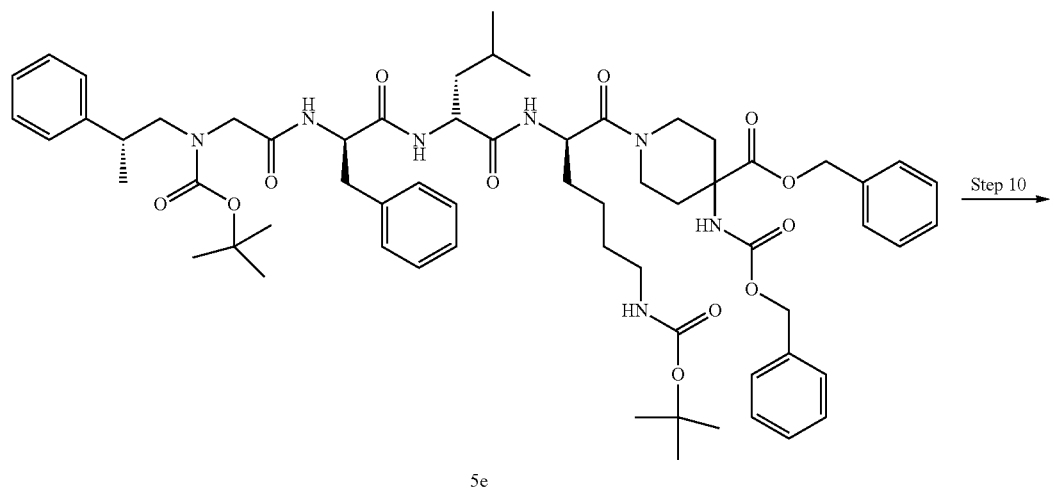
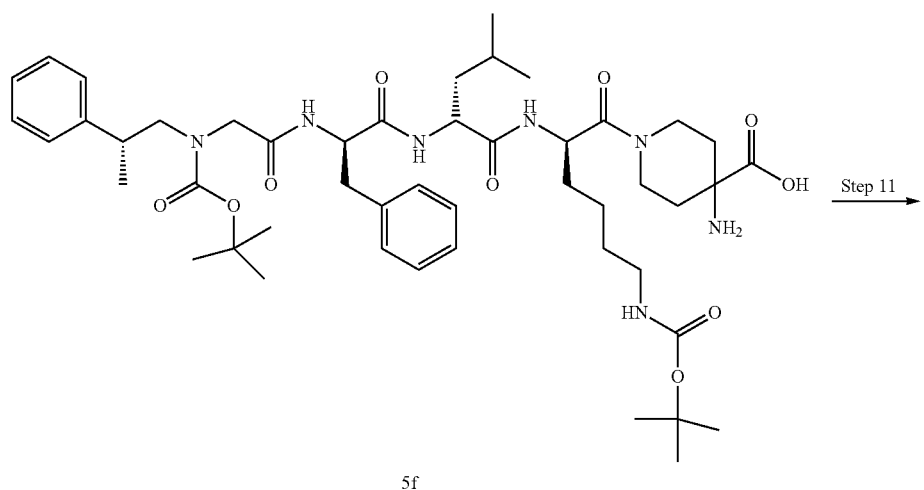

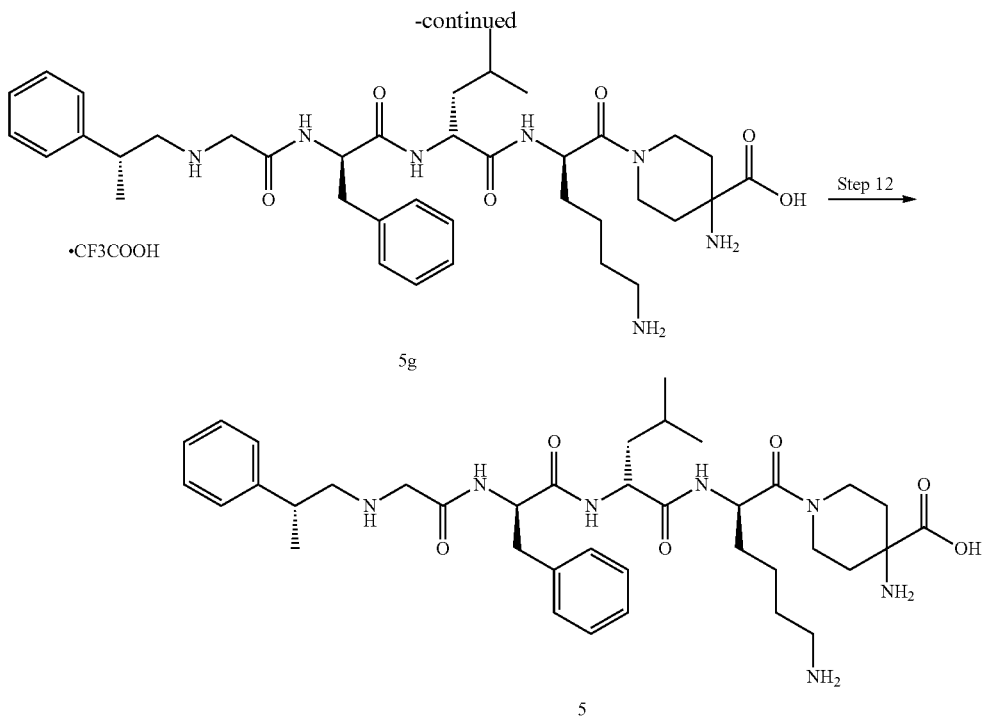

4-Benzyl 1-tert-butyl 4-(((benzyloxy)carbonyl) amino)piperidine-1,4-dicarboxylate 1b 4-(((Benzyloxy)carbonyl) amino)-1-(tert-butoxycarbonyl)piperidine-4-carboxylic acid 1a (1.2 g, 0.0032 mol, prepared by a known method disclosed in "*Bioorganic Medicinal Chemistry Letters,* 2007, 7(9), 2448-2451"), benzyl bromide (0.65 g, 0.0038 mol) and cesium carbonate (2.1 g, 0.0064 mol) were dissolved in 20 mL of N,N-dimethylformamide, and stirred for 12 hours at room temperature. The reaction solution was poured into water and extracted with ethyl acetate (30 mL×3). The organic phases were combined, dried over anhydrous sodium sulfate and filtered. The filtrate was concentrated under reduced pressure, and the resulting residue was purified by thin layer chromatography with elution system B to obtain the title compound 1b (800 mg, a colorless viscous substance, yield: 53%).

Step 2

Benzyl 4-(((benzyloxy)carbonyl)amino)piperidine-4-carboxylate hydrochloride 1c Compound 1b (800 mg, 1.71 mmol) was dissolved in 2 mL of dichloromethane, and 2 mL of a solution of 4M hydrochloric acid in 1,4-dioxane was added. After stirring for 4 hours at room temperature, the reaction solution was concentrated under reduced pressure to obtain the crude title compound 1c (800 mg, a light yellow viscous substance), which was used directly in the next step without purification.

Step 3

(R)-Benzyl 1-(2-((((9H-fluoren-9-yl)methoxy)carbonyl)amino)-6-((tert-butoxycarbonyl)amino) hexanoyl)-4-(((benzyloxy)carbonyl)amino)piperidine-4-carboxylate 1e The crude compound 1c (800 mg, 1.97 mmol) and (R)-2-((((9H-fluoren-9-yl)methoxy)carbonyl)amino)-6-((tert-butoxycarbonyl)amino)hexanoic acid 1d (926 mg, 1.97 mmol, prepared by a known method disclosed in "*ChemMedChem,* 2015, 10(7), 1232-1239") were dissolved in 20 mL of N,N-dimethylformamide. 2-(7-azabenzotriazol)-N,N,N',N'-tetramethyluronium hexafluorophosphate (1.12 g, 3.0 mmol) and N,N-diisopropylethylamine (0.7 mL, 3.94 mmol) were added. After stirring for 12 hours at room temperature, the reaction solution was poured into 2N citric acid solution and extracted with ethyl acetate (30 mL×3). The organic phases were combined, washed with saturated sodium bicarbonate solution, dried over anhydrous sodium sulfate and filtered. The filtrate was concentrated under reduced pressure to obtain the crude title compound 1e (1.6 g, a yellow viscous substance), which was used directly in the next step without purification.

Step 4

(R)-Benzyl 1-(2-amino-6-((tert-butoxycarbonyl) amino)hexanoyl)-4-(((benzyloxy) carbonyl)amino) piperidine-4-carboxylate 1f The crude compound 1e (1.6 g, 0.002 mol) was dissolved in 10 mL of dichloromethane, and then 10 mL of piperidine was added. After stirring for 2 hours at room temperature, the reaction solution was concentrated under reduced pressure. The resulting residue was purified by thin layer chromatography with elution system A to obtain the title compound 1f (900 mg, a light yellow solid, yield: 77%).

Step 5

(R)-Benzyl 2-((R)-2-(2-chloroacetamido)-3-phenylpropionamido)-4-methylpentanoate 1i (R)-Benzyl 2-((R)-2-amino-3-phenylpropanamido)-4-methylpentanoate 1g (500 mg, 1.36 mmol, prepared by a method disclosed in the patent application "US20110212882A1") and triethylamine (275 mg, 2.72 mmol) were dissolved in 10 mL of dichloromethane, and then chloroacetyl chloride (230 mg, 2 mmol) was added dropwise. After stirring for 12 hours at room temperature, the reaction solution was poured into water and washed with saturated ammonium chloride solution. The organic phase was dried over anhydrous sodium sulfate, and filtered. The filtrate was concentrated under reduced pressure to obtain the crude title product 1i (500 mg, a yellow viscous substance), which was used directly in the next step without purification.

Step 6

(R)-Benzyl 4-methyl-2-((R)-3-phenyl-2-(2-(((R)-2-phenylpropyl)amino)acetamido)propanamido)pentanoate 5b Compound 1i (500 mg, 1.12 mmol) and (R)-2-phenylpropan-1-amine 5a (228 mg, 1.68 mmol, prepared by a known method disclosed in "*Angewandte Chemie, International Edition*, 2003, 42(39), 4793-4795") were dissolved in 10 mL of N,N-dimethylformamide, and then potassium iodide (372 mg, 2.24 mmol) and potassium carbonate (309 mg, 2.24 mmol) were added. The reaction solution was warmed up to 60° C. and stirred for 12 hours. The reaction solution was cooled to room temperature, added with water, and extracted with dichloromethane (30 mL×3). The organic phases were combined, dried over anhydrous sodium sulfate and filtered. The filtrate was concentrated under reduced pressure to obtain the crude title compound 5b (600 mg, a brown viscous substance), which was used directly in the next step without purification.

Step 7

(9R,12R)-Benzyl 9-benzyl-12-isobutyl-2,2-dimethyl-4,7,10-trioxo-5-((R)-2-phenylpropyl)-3-oxa-5, 8,11-triazatridecan-13-oate 5c The crude compound 5b (600 mg, 1.1 mmol) was dissolved in 20 mL of dichloromethane, and then di-tert-butyl dicarbonate (361 mg, 1.66 mmol) and triethylamine (222 mg, 2.2 mmol) were added. After stirring for 12 hours at room temperature, the reaction solution was concentrated under reduced pressure. The resulting residue was purified by thin layer chromatography with elution system A to obtain the title compound 5c (580 mg, a light yellow viscous substance, yield: 82%).

Step 8

(9R,12R)-9-benzyl-12-isobutyl-2,2-dimethyl-4,7,10-trioxo-5-((R)-2-phenylpropyl)-3-oxa-5,8,11-triazatridecan-13-oic acid 5d Compound 5c (580 mg, 0.9 mmol) was dissolved in 10 mL of methanol, and then palladium-carbon (60 mg, catalytic amount) was added. After completion of the addition, the reaction system was purged with hydrogen three times and stirred for 12 hours at room temperature. The reaction solution was filtered through celite, and the filtrate was concentrated under reduced pressure to obtain the crude title compound 5d (500 mg, a light yellow viscous substance), which was used directly in next step without purification.

Step 9

Benzyl 1-((9R,12R,15R)-9-benzyl-15-(4-((tert-butoxycarbonyl)amino)butyl)-12-isobutyl-2,2-dimethyl-4,7,10,13-tetraoxo-5-((R)-2-phenylpropyl)-3-oxa-5,8,11,14-tetraazahexadecan-16-oyl)-4-(((benzyloxy)carbonyl)amino)piperidine-4-carboxylate 5e The crude compound 5d (365 mg, 0.66 mmol), if (393 mg, 0.66 mmol), 2-(7-azabenzotriazol)-N,N,N',N'-tetramethyluronium hexafluorophosphate (376 mg, 0.99 mmol) and N,N-diisopropylethylamine (0.16 mL, 0.99 mmol) were dissolved in 10 mL of N,N-dimethylformamide. After stirring for 2 hours at room temperature, the reaction solution was concentrated under reduced pressure. The resulting residue was purified by thin layer chromatography with elution system A to obtain the title compound 5e (170 mg, a light yellow solid, yield: 23%).

Step 10

4-Amino-1-((9R,12R,15R)-9-benzyl-15-(4-((tert-butoxycarbonyl)amino)butyl)-12-isobutyl-2,2-dimethyl-4,7,10,13-tetraoxo-5-((R)-2-phenylpropyl)-3-oxa-5,8,11,14-tetraazahexadecan-16-oyl)piperidine-4-carboxylic acid 5f Compound 5e (80 mg, 0.0706 mmol) was dissolved in 10 mL of methanol, then palladium-carbon (10 mg, catalytic amount) was added. After completion of the addition, the reaction system was purged with hydrogen three times and stirred for 12 hours at room temperature. The reaction solution was filtered through celite, and the filtrate was concentrated under reduced pressure to obtain the crude title compound 5f (60 mg, a white solid), which was used directly in the next step without purification.

Step 11

4-Amino-1-((2R,5R,8R,14R)-2-(4-aminobutyl)-8-benzyl-5-isobutyl-4,7,10-trioxo-14-phenyl-3,6,9,12-tetraazapentadecan-1-oyl)piperidine-4-carboxylic acid trifluoroacetate 5g The crude product 5f (60 mg, 0.066 mmol) was dissolved in 2 mL of dichloromethane, and then 1 mL of a solution of 4M hydrochloric acid in 1,4-dioxane was added. After stirring for 2 hours at room temperature, the reaction solution was concentrated under reduced pressure. The resulting residue was purified by high performance liquid chromatography to obtain the title compound 5g (30 mg, a white solid).

MS m/z (ESI): 708.6 [M+1]

Step 12

4-Amino-1-((2R,5R,8R,14R)-2-(4-aminobutyl)-8-benzyl-5-isobutyl-4,7,10-trioxo-14-phenyl-3,6,9,12-tetraazapentadecan-1-oyl)piperidine-4-carboxylic acid 5

Compound 5g (30 mg, 0.028 mmol) was dissolved by 5 mL of a mixed solvent of methanol/water (V:V=10:1), and then sodium bicarbonate solid (10 mg) was added to adjust the pH to 7. The reaction solution was stirred for 30 minutes, and then was concentrated under reduced pressure. The resulting residue was added with 10 mL of dichloromethane, stirred for 30 minutes, and filtered. The filter cake was rinsed with 10 mL of dichloromethane, and the filtrate was concentrated under reduced pressure to obtain the title compound 5 (17 mg, a white solid).

MS m/z (ESI): 708.6 [M+1]

$^1$H NMR (400 MHz, CD$_3$OD): δ 7.33-7.19 (m, 10H), 4.90-4.84 (m, 2H), 4.64-4.61 (m, 2H), 4.42-4.39 (m, 1H), 3.86-3.74 (m, 5H), 3.20-3.12 (m, 4H), 2.94-2.84 (m, 4H), 2.61-2.54 (m, 2H), 2.20-2.15 (m, 3H), 1.79-1.70 (m, 2H), 1.68-1.60 (m, 8H), 1.45-1.40 (m, 3H), 1.30-1.20 (m, 5H), 0.99-0.76 (m, 6H).

Example 2. Preparation of Compound 20

The apparatus, equipment and materials required for the preparation of compound 20 are shown in Example 1.

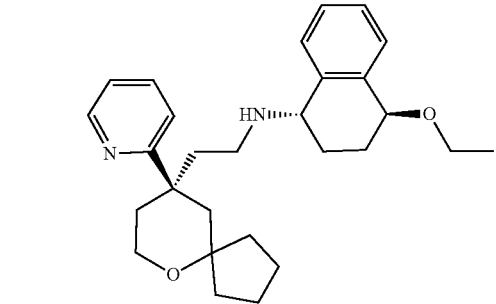

(1S,4S)-4-Ethoxy-N-(2-((R)-9-(pyridin-2-yl)-6-oxaspiro[4.5]decan-9-yl)ethyl)-1,2,3,4-tetrahydronaphthalen-1-amine

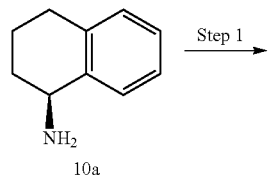

10a

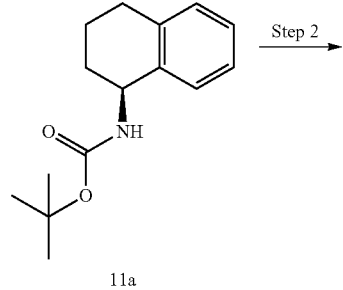

11a

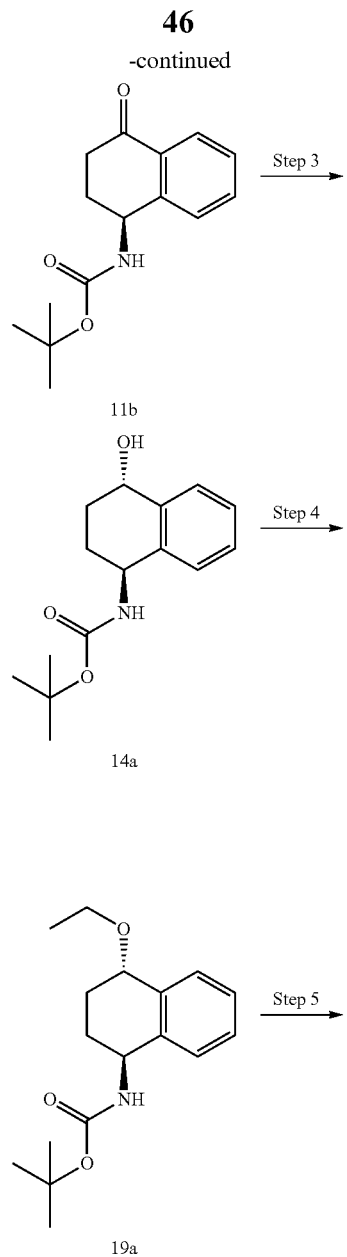

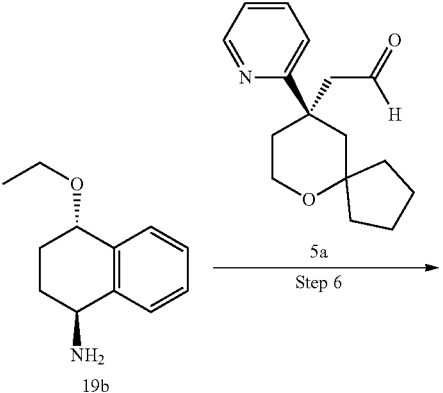

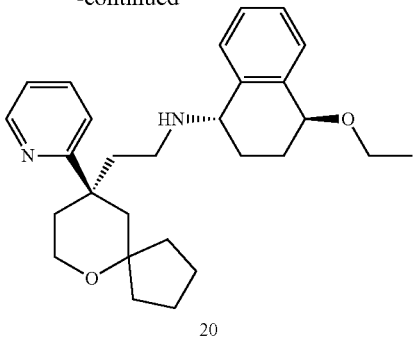

(S)-Tert-butyl (1,2,3,4-tetrahydronaphthalen-1-yl)carbamate 11a (S)-1,2,3,4-Tetrahydronaphthalen-1-amine 10a (3 g, 20.41 mmol, prepared according to the known method disclosed in "*Angewandte Chemie-International Edition*, 45(28), 4641-4644, 2006") was dissolved in 100 mL of dichloromethane, and then triethylamine (5.7 mL, 40.82 mmol) and di-tert-butyl dicarbonate (4.9 g, 22.45 mmol) were added. After stirring for 12 hours, the reaction solution was washed successively with water (100 mL) and saturated sodium bicarbonate solution (100 mL). The organic phase was dried over anhydrous sodium sulfate and filtered. The filtrate was concentrated under reduced pressure to obtain the crude title product 11a (5.6 g) as a light yellow oil, which was used directly in the next step without purification.

MS m/z (ESI): 248.3 [M+1]

Step 2

(S)-Tert-butyl (4-oxo-1,2,3,4-tetrahydronaphthalen-1-yl)carbamate 11b

The crude (S)-tert-butyl (1,2,3,4-tetrahydronaphthalen-1-yl)carbamate 11a (5.6 g, 20.41 mmol) was dissolved in 90 mL of a mixed solution of acetone and water (V/V=2:1), and then magnesium sulfate (5.5 g, 45.66 mmol) was added and potassium permanganate (7.22 g, 45.66 mmol) was slowly added with stirring. The reaction system was stirred for 12 hours. Then, the reaction solution was concentrated under reduced pressure, and the resulting residue was purified by silica gel column chromtography with n-hexane/ethyl acetate system to obtain the title product 11b (3.1 g, yield 52%) as an off-white solid.

MS m/z (ESI): 262.3 [M+1]

Step 3

Tert-butyl ((1S,4S)-4-hydroxy-1,2,3,4-tetrahydronaphthalen-1-yl)carbamate 14a (S)-Tert-butyl (4-oxo-1,2,3,4-tetrahydronaphthalen-1-yl)carbamate 11b (100 mg, 0.883 mmol) was dissolved in 5 mL of toluene. The reaction solution was cooled to 0° C., added with (R)-2-methyl-CBS-oxazaborolidine (0.1 ml, 0.076 mmol), and stirred for 5 minutes. Then, borane methylsulfide (0.88 ml, 0.76 mmol) was added, and the reaction was stirred for 2 hours. The reaction was quenched by adding 50 ml of saturated sodium chloride solution, and extracted with ethyl acetate (30 mL×3). The organic phases were combined, washed with saturated sodium chloride solution (30 mL×3), dried over anhydrous sodium sulfate and filtered. The filtrate was concentrated under reduced pressure, and the resulting residue was purified by thin layer chromtography with dichloromethane/methanol system to obtain the title product 14a (60 mg, yield 60%) as a white solid.

MS m/z (ESI): 208.3 [M−55]

Step 2

Tert-butyl ((1S,4S)-4-ethoxy-1,2,3,4-tetrahydronaphthalen-1-yl)carbamate 19a The crude tert-butyl ((1S)-4-hydroxy-1,2,3,4-tetrahydronaphthalen-1-yl) carbamate 14a (850 mg, 3.23 mmol), silver oxide (76 mg, 0.33 mmol) and iodoethane (1.3 mL, 16.15 mmol) were dissolved in 30 mL of dichloromethane, and the reaction solution was stirred for 48 hours. The reaction solution was filtered, and the filtrate was concentrated under reduced pressure to obtain the crude title product 19a (800 mg) as a yellow oil, which was used directly in the next step without purification.

MS m/z (ESI): 236.1 [M−55]

Step 3

(1S,4S)-4-Ethoxy-1,2,3,4-tetrahydronaphthalen-1-amine 19b

The crude compound 19a (698 mg, 2.4 mmol) was dissolved in 4 mL of dichloromethane, and then 8 mL of a solution of 4 M hydrogen chloride in 1,4-dioxane were added. After stirring for 2 hours, the reaction solution was concentrated under reduced pressure, triturated with ethyl acetate (30 mL) and filtered. The filter cake was dissolved in 20 mL of a mixed solution of dichoromethane and methanol (V:V=5:1). Saturated sodium bicarbonate solution was added to adjust the pH of the reaction solution to 7 to 8. The reaction solution was concentrated under reduced pressure, washed with a mixed solution of dichloromethane and methanol (V:V=5:1) (30 mL×2) and filtered. The filtrate was concentrated under reduced pressure to obtain the crude title product 19b (310 mg) as a yellow liquid, which was used directly in next step without purification.

MS m/z (ESI): 191.1 [M+1]

Step 4

(1S,4S)-4-Ethoxy-N-(2-((R)-9-(pyridin-2-yl)-6-oxaspiro[4.5]decan-9-yl)ethyl)-1,2,3,4-tetrahydronaphthalen-1-amine 20

(R)-2-(9-(Pyridin-2-yl)-6-oxaspiro[4.5]decan-9-yl)acetaldehyde 5a (500 mg, 1.85 mmol, prepared according to the method disclosed in the patent application "WO2012129495") and the crude compound 19b (310 mg, 1.85 mmol) were dissolved in 30 mL of dichloromethane, and the mixture was stirred for 40 minutes, and then sodium triacetoxyborohydribe (980 mg, 4.63 mmol) was added. After stirring for 2 hours, the reaction solution was washed successively with saturated sodium bicarbonate solution (30 mL×3) and saturated sodium chloride solution (30 mL×3). The organic phase was dried over anhydrous sodium sulfate and filtered. The filtrate was concentrated under reduced pressure, and the resulting residue was purified by thin layer chromatography with dichloromethane/methanol system to obtain the title product 20 (280 mg, yield 35%) as a yellow viscous solid.

MS m/z (ESI): 435.3 [M+1]

$^1$H NMR (400 MHz, CDCl$_3$) δ 9.74 (d, 1H), 9.58 (d, 1H), 8.94 (d, 1H), 8.37 (d, 1H), 7.94 (d, 1H), 7.67 (d, 1H), 7.52 (d, 1H), 7.47 (t, 1H), 4.46-4.49 (m, 1H), 4.30-4.33 (m, 1H), 3.84-3.87 (m, 1H), 3.66-3.70 (m, 2H), 3.53-3.56 (m, 2H), 2.82-2.85 (d, 2H), 2.67 (s, 2H), 2.39-2.41 (m, 4H), 2.30-2.33 (m, 4H), 1.85 (s, 2H), 1.48-1.52 (m, 6H), 1.27 (m, 3H).

Example 3. Treatment Effect of the Combination of the KOR Agonist and the MOR Agonist of the Present Invention on Incision Pain in Rats Test Compounds Compound 5 (prepared according to the method described in Example 1), and compound 20 (prepared according to the method described in Example 2). The compound dose was calculated on bases.

Test Animals

Experimental male Wistar rats were purchased from Shanghai Slac Laboratory Animal Co., Ltd. The rats weighed 140-160 g when purchased, and were fed at 5 rats/cage, under a condition of 12/12 hours light/dark cycle adjustment, a constant temperature of 23±1° C., a humidity of 50-60%, and free access to food and water. After purchase, the animals were subjected to an adaptive feeding for more than 3 days before the experiment was started.

Experimental Apparatus

Electronic Von Frey: UGO BASILE, type 38450.

Formulation of the Solution of the Test Compound

Both compound 5 and compound 20 were formulated with normal saline.

Test Method

The rats were randomly divided into the following groups according to the body weight: blank control group (n=10), model group (n=10) and drug-administered group (n=50). The drug-administered group was divided into the following groups: compound 20-0.03 mg/kg group (n=10), compound 5-0.3 mg/kg group (n=10), compound 5-0.1 mg/kg+compound 20-0.03 mg/kg group (n=10), compound 5-0.3 mg/kg+compound 20-0.03 mg/kg group (n=10), and compound 5-1 mg/kg+compound 20-0.03 mg/kg group (n=10). The model group and drug-administered group were subjected to an incision surgery. During the surgery, the rats were anesthetized with isoflurane. An incision (1 cm long) passing through the skin and fascia was made with a No. 10 surgical blade in the middle of the left hind paw. The skin was sutured with a 3-0 sterile silk surgical suture. The injured site was disinfected with antibiotic ointment and iodophor. The animals were returned to their original place to recover overnight. After 24 hours, the drug was injected through the tail vein, and the blank control group and the model group were administrated with normal saline two times with an interval of 15 minutes. The group administered with compound 20 alone was intravenously injected with the corresponding dose of compound 20 and the blank solvent for formulating compound 5. The group administered with compound 5 alone was intravenously injected with the corresponding dose of compound 5 and the blank solvent for formulating compound 20. The group administered with the combination was intravenously injected with the corresponding dose of compound 5, and then intravenously injected with the corresponding dose of compound 20 after 15 minutes. The mechanical pain threshold of each group was measured by the Electronic Von Frey 30 minutes after the injection to evaluate the analgesic effect of the drug on the surgical incision pain and the intensity thereof.

Data Representation and Statistical Processing

The experimental data were expressed as mean±standard deviation (S.D.). Statistical comparisons were performed using t test in the Excel software. The data between the model group and the blank control group were analyzed and compared to determine whether there was a significant statistical difference or not. #P<0.05 indicates that there is a significant difference between the model group and the blank control group, and ##P<0.01 indicates that there is a highly significant difference between the model group and the blank control group. ΔP<0.05 indicates that there is a significant difference between the drug-administered group and the model group, and ΔΔP<0.01 indicates that there is a highly significant difference between the drug-administered group and the model group. *P<0.05 indicates that there is a significant difference between the drug-combination-administered group and the single-drug-administered group, and **P<0.01 indicates that there is a highly significant difference between the drug-combination-administered group and the single-drug-administered group.

Experimental Results

The results are shown in FIG. 1.

Experimental Conclusion

The experimental results (FIG. 1, mpk is the abbreviation of mg/kg) showed that the tenderness threshold of the blank control group of the rats was 14.48 g, and the tenderness threshold of the model group was 8.91 g. Compared with the blank control group, the tenderness threshold of the model group was significantly decreased (P<0.05). After the drug administration, compared with the model group, the tenderness threshold of the compound 20-0.03 mg/kg group was significantly increased (P<0.01) to 14.46 g, with an increase of 62.3%; the tenderness threshold of the compound 5-0.3 mg/kg group was significantly increased (P<0.01) to 17.92 g, with an increase of 101.1%.

Compared with the model group, the combination of compound 20-0.03 mg/kg and compound 5-0.1 mg/kg, compound 5-0.3 mg/kg or compound 5-1 mg/kg all can significantly increase (P<0.01) the tenderness threshold of rats to 17.96 g, 22.29 g or 33.46 g, with an increase of 101.6%, 150.1% or 275.5%, respectively, indicating the dose-effect relationship of KOR agonist. The combined effects with three doses were better than the effect of compound 20-0.03 mg/kg alone. The combination of compound 20-0.03 mg/kg and compound 5-0.3 mg/kg or compound 5-1 mg/kg had a statistical difference (P<0.01).

Compared with compound 5-0.3 mg/kg alone, the combination of compound 20-0.03 mg/kg+compound 5-0.1 mg/kg had an equivalent increase of tenderness threshold. The combined effects of compound 20-0.03 mg/kg and compound 5-0.3 mg/kg or compound 5-1 mg/kg were better than the effect of compound 5-0.3 mg/kg alone. The combination of compound 20-0.03 mg/kg and compound 5-1 mg/kg had a statistical difference (P<0.01).

In summary, the administration of compound 20-0.03 mg/kg alone or compound 5-0.3 mg/kg alone to the rat had a good effect of decreasing incision pain (P<0.01). In addition, the test results of the combined administration group showed that compound 20 and compound 5 had a synergistic effect, and the effect of the combination of compound 20 and compound 5 was better than that of the compound administered alone at the same dose.

What is claimed is:

1. A method of alleviating and/or treating pain in a subject in need thereof, comprising administering to the subject a therapeutically effective amount of a pharmaceutical composition comprising a κ opioid receptor (KOR) agonist and μ opioid receptor (MOR) agonist, wherein the KOR agonist is a compound of formula (I):

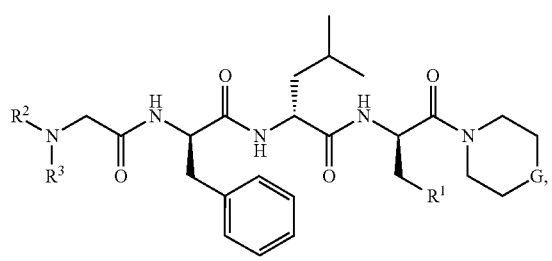

or a tautomer, mesomer, racemate, enantiomer, or diastereomer thereof, or a mixture thereof, or a pharmaceutically acceptable salt thereof, wherein:

G is selected from the group consisting of O, —NR$^4$ and —CR$^5$R$^6$;

R$^1$ is selected from the group consisting of hydrogen, alkyl, alkoxy, haloalkyl, halogen, amino, nitro, hydroxy, cyano, cycloalkyl, heterocyclyl, aryl, heteroaryl, —OR$^7$, —C(O)R$^7$, —C(O)OR$^7$, —S(O)$_m$R$^7$ and —NR$^8$R$^9$, wherein the alkyl, haloalkyl, cycloalkyl, heterocyclyl, aryl and heteroaryl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

R$^2$ is selected from the group consisting of hydrogen, alkyl, alkoxy, haloalkyl, cycloalkyl, cycloalkylalkyl, heterocyclyl, heterocyclylalkyl, aryl, arylalkyl, heteroaryl, heteroarylalkyl, —OR$^7$, —C(O)R$^7$ and —C(O)OR$^7$, wherein the alkyl, haloalkyl, cycloalkyl, cycloalkylalkyl, heterocyclyl, heterocyclylalkyl, aryl, arylalkyl, heteroaryl and heteroarylalkyl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

R$^3$ is selected from the group consisting of hydrogen, alkyl, alkoxy, haloalkyl, cycloalkyl, cycloalkylalkyl, heterocyclyl, heterocyclylalkyl, aryl, arylalkyl, heteroaryl, heteroarylalkyl, —OR$^7$, —C(O)R$^7$ and —C(O)OR$^7$, wherein the alkyl, haloalkyl, cycloalkyl, cycloalkylalkyl, heterocyclyl, heterocyclylalkyl, aryl, arylalkyl, heteroaryl and heteroarylalkyl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

R$^4$ is selected from the group consisting of hydrogen, alkyl, haloalkyl, cycloalkyl, alkoxy, hydroxyalkyl, amino, alkoxycarbonyl, heterocyclyl, aryl, heteroaryl, —OR$^7$, —C(O)R$^7$, —C(O)OR$^7$, —S(O)$_m$R$^7$, —NR$^8$R$^9$ and —NHC(O)NR$^8$R$^9$, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

R$^5$ and R$^6$ are each independently selected from the group consisting of hydrogen, alkyl, alkoxy, hydroxyalkyl, hydroxy, amino, alkoxycarbonyl, cycloalkyl, heterocyclyl, aryl, heteroaryl, —OR$^7$, —C(O)R$^7$, —C(O)OR$^7$, —S(O)$_m$R$^7$, —NR$^8$R$^9$ and —NHC(O)NR$^8$R$^9$, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

R$^7$ is selected from the group consisting of hydrogen, alkyl, amino, alkoxy, hydroxyalkyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, nitro, cyano, alkoxy, hydroxyalkyl, cycloalkyl, heterocyclyl, aryl and heteroaryl;

R$^8$ and R$^9$ are each independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl; and m is 0, 1 or 2.

2. The method according to claim 1, wherein the KOR agonist is a compound of formula (I-B):

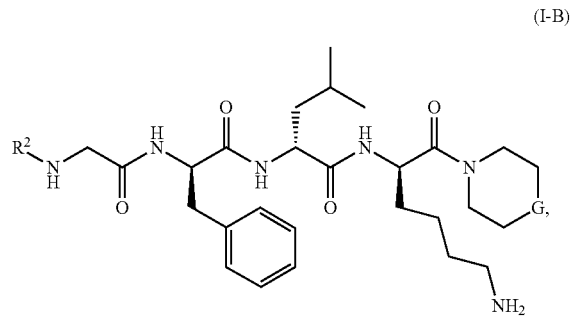

or diastereomer thereof, or a mixture thereof, or a pharmaceutically acceptable salt thereof.

3. The method according to claim 1, wherein the KOR agonist is a compound of formula (I-C):

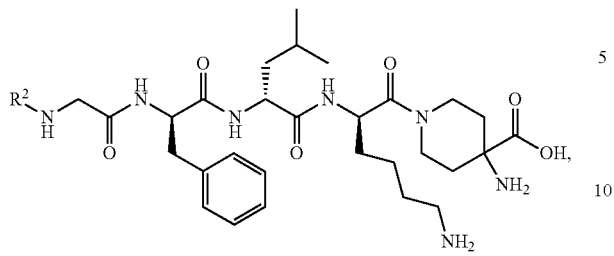
or diastereomer thereof, or a mixture thereof, or a pharmaceutically acceptable salt thereof.
4. The method according to claim 1, wherein the KOR agonist is selected from the group consisting of:
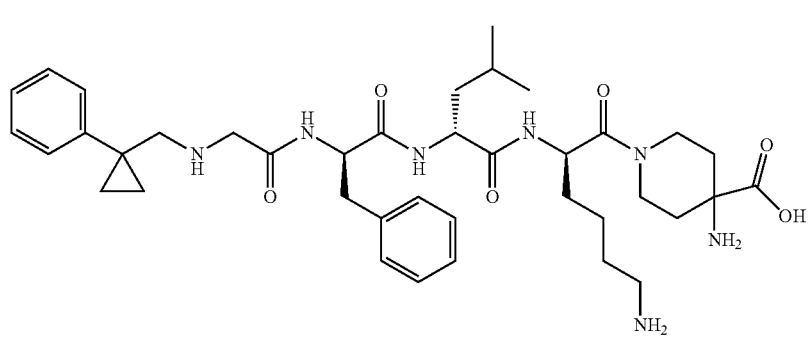
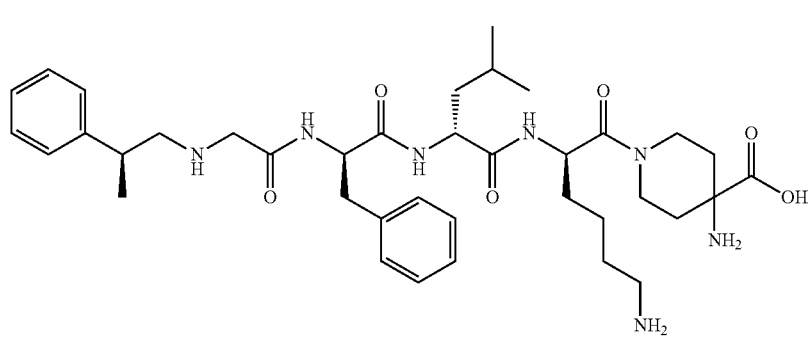
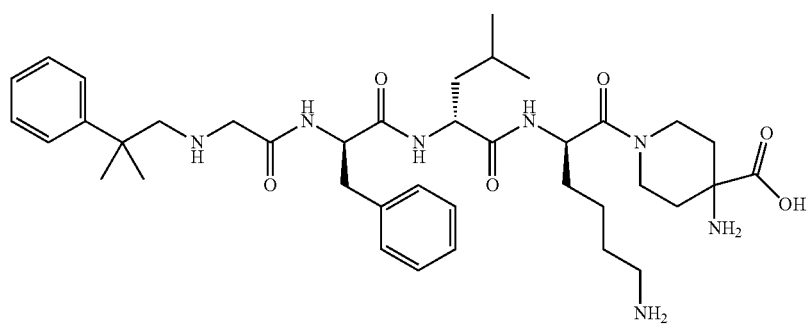

4
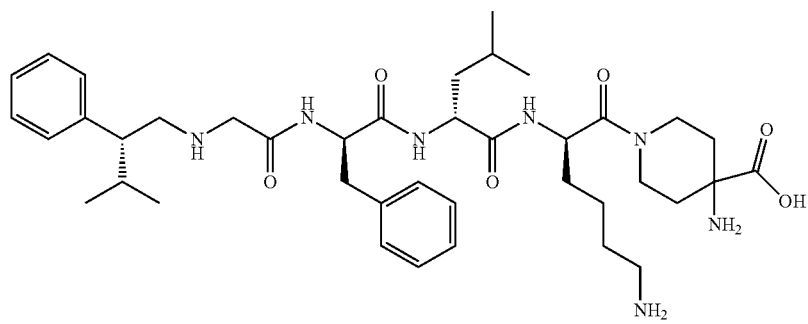
5
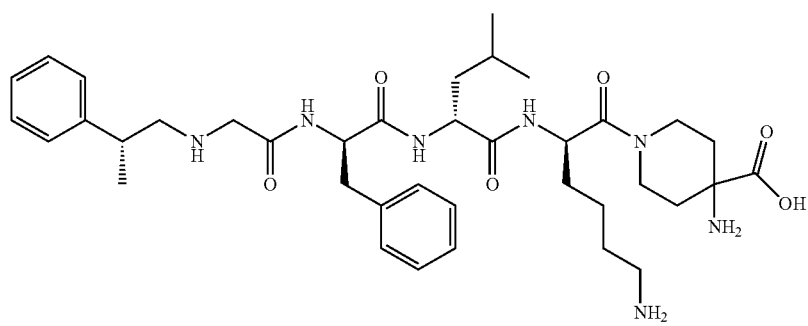
6
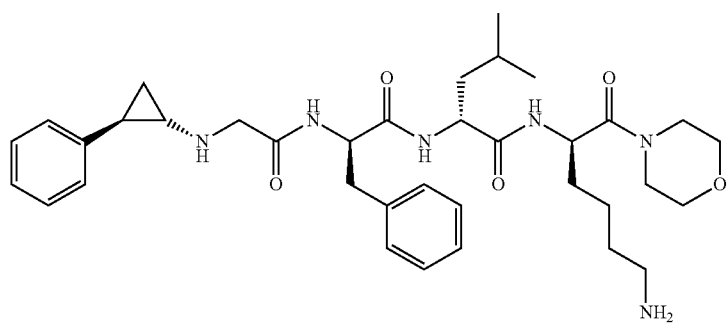
7
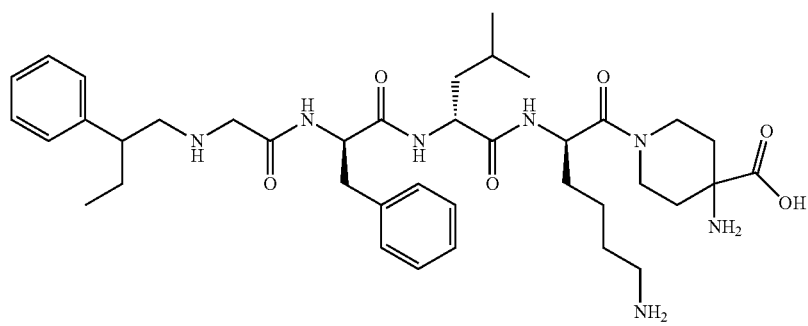
8
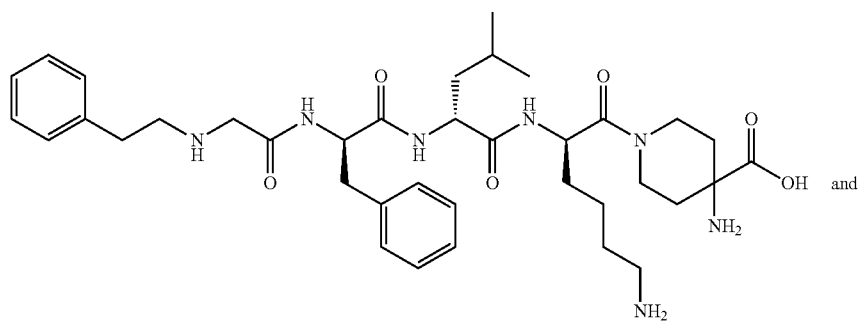
and

-continued

9

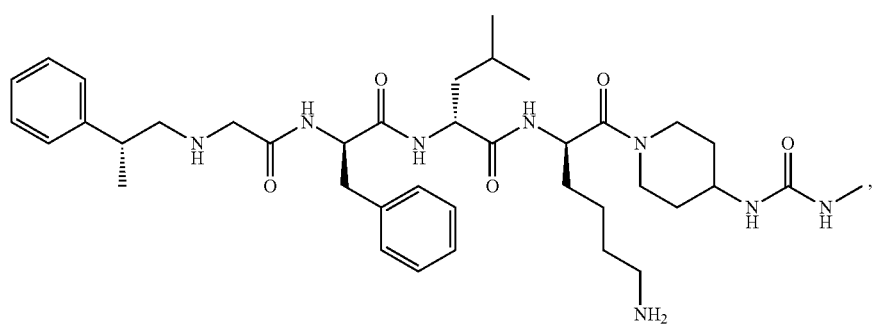

or a tautomer, mesomer, racemate, enantiomer, or diastereomer thereof, or a mixture thereof, or a pharmaceutically acceptable salt thereof.

5. The method according to claim 1, wherein the MOR agonist is a compound of formula (II):

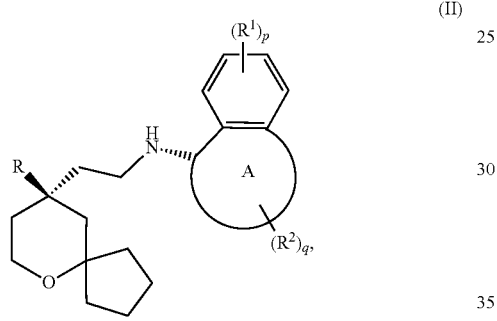

(II)

or a tautomer, mesomer, racemate, enantiomer, or diastereomer thereof, or a mixture thereof, or a pharmaceutically acceptable salt thereof,
wherein:
ring A is selected from the group consisting of cycloalkyl and heterocyclyl;
R is selected from the group consisting of aryl and heteroaryl, wherein the aryl and heteroaryl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl, heteroaryl, —$OR^3$, —$C(O)R^3$, —$C(O)OR^3$, —$S(O)_mR^3$ and —$NR^4R^5$;
each $R^1$ is identical or different and each is independently selected from the group consisting of hydrogen, alkyl, alkoxy, haloalkyl, halogen, amino, nitro, hydroxy, cyano, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, haloalkyl, cycloalkyl, heterocyclyl, aryl and heteroaryl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;
each $R^2$ is identical or different and each is independently selected from the group consisting of hydrogen, alkyl, alkoxy, haloalkyl, halogen, amino, nitro, hydroxy, cyano, oxo, alkenyl, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, alkoxy, alkenyl, haloalkyl, cycloalkyl, heterocyclyl, aryl and heteroaryl are each optionally substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl and heteroaryl;
or two $R^2$ are taken together to form a cycloalkyl or heterocyclyl, wherein the cycloalkyl or heterocyclyl is optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;
$R^3$ is selected from the group consisting of hydrogen, alkyl, deuterated alkyl, amino, alkoxy, hydroxyalkyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, nitro, cyano, alkoxy, hydroxyalkyl, cycloalkyl, heterocyclyl, aryl and heteroaryl;
$R^4$ and $R^5$ are each independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;
p and q are each independently 0, 1, 2, 3 or 4; and
m is 0, 1 or 2.

6. The method according to claim 5, wherein the MOR agonist is a compound of formula (II-B):

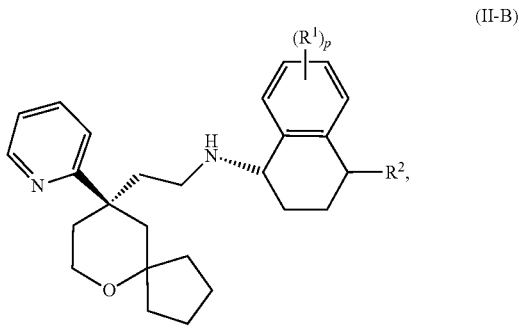

(II-B)

or diastereomer thereof, or a mixture thereof, or a pharmaceutically acceptable salt thereof.

7. The method according to claim 5, wherein the MOR agonist is selected from the group consisting of:
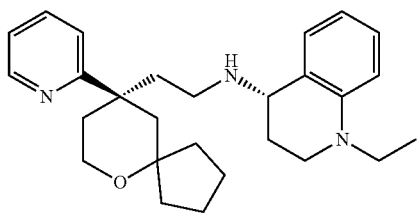
10
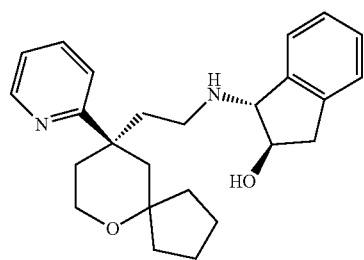
11
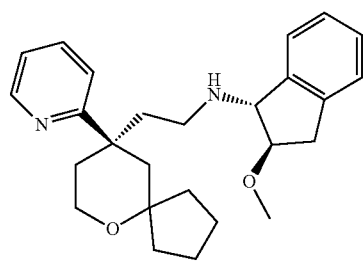
12
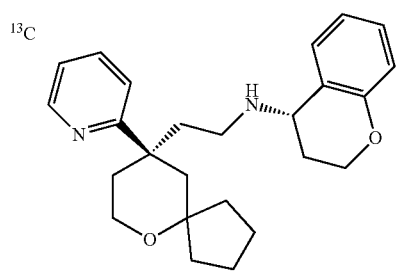
13
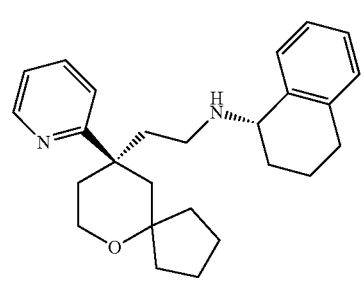
14
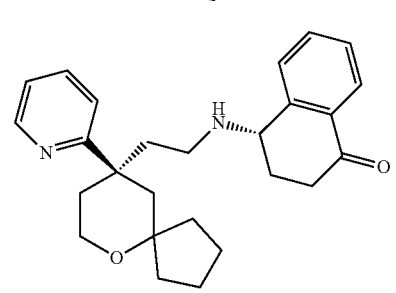
15
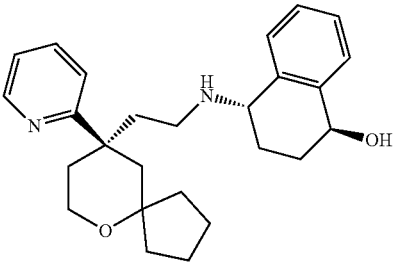
16
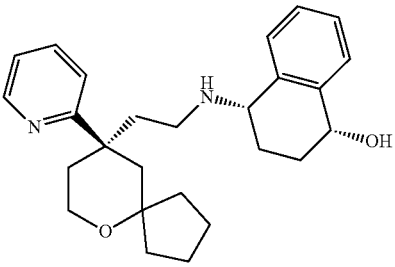
17
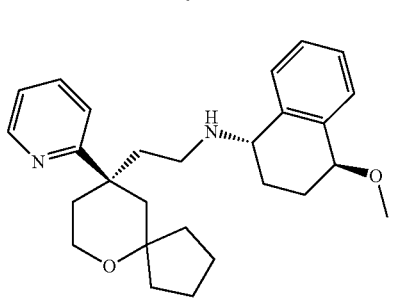
18
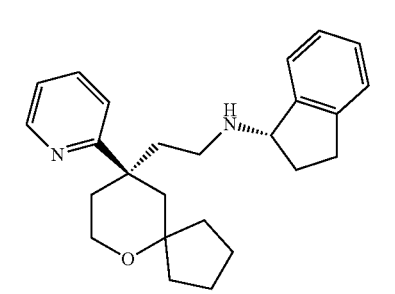
19
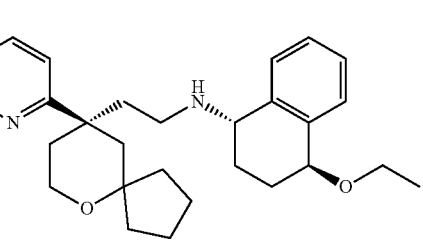
20
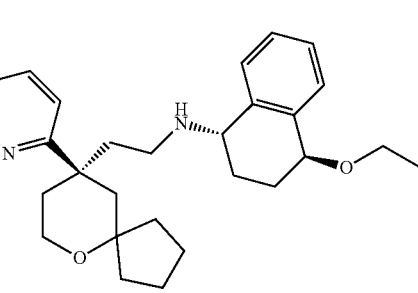
21

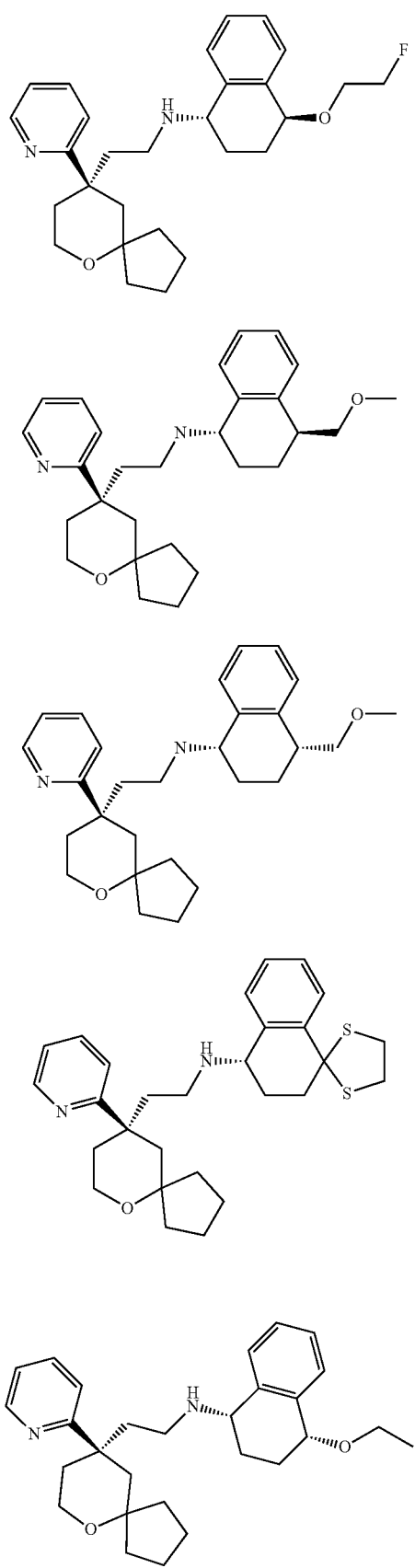
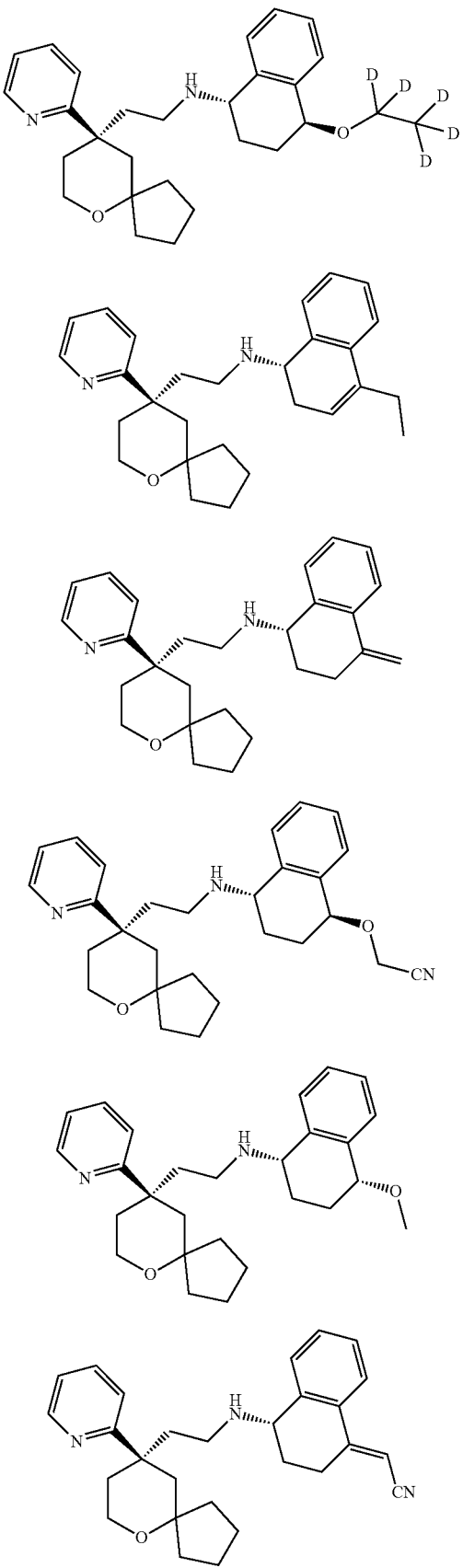

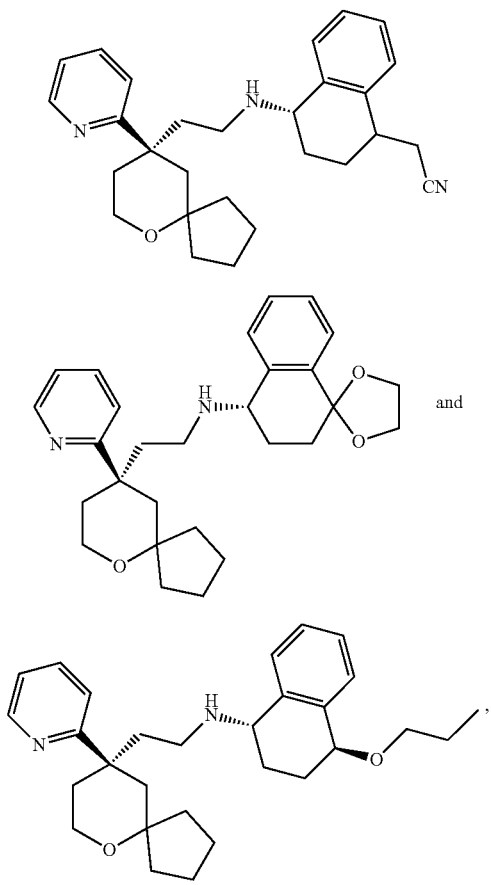

or a tautomer, mesomer, racemate, enantiomer, or diastereomer thereof, or a mixture thereof, or a pharmaceutically acceptable salt thereof.

8. The method according to claim 1, wherein the MOR agonist is selected from the group consisting of dihydromorphone hydrochloride, morphine, oxycodone, buprenorphine, sufentanil, fentanyl, trifentanil, remifentanil, tapentadol, NKTR-181, eluxadoline, benzohydrocodone, loperamide, oliceridine, samidorphan, cebranopadol, tapentadol, methadone, tramadol, TV-46763, hydrocodone, dexketoprofen, oxymorphone, MH-200, levorphanol, Sedatin, desmethyl tramadol, IBCh-07, HS-731, Cyt-1010, trimebutine 3-thiocarbamoyl-benzenesulfonate, thienorphine, trimebutine, TRV-734, TRK-130, hydromorphone, hydromorphone prodrug, EU-178, OREX-1038, AIKO-152, TH-030418, CC-408, XE-440, CYX-6, Org-41793, DPI-125, KN-203, JVA-3025, AT-121, VRP-26, endomorphin, NKTR-196, NKTR-174, NKTR-192, NESS-117-OPB, SYK-524, HS-731, HS-198, Dmt-Tic analogue, endorphin 1 derivative, MMP-2200, SEO-16, TLI-0326, BU-08028, BU-08073, TLI-1186, KIN-3031, Neo-1509, GRT-6006, MCP-201, NE-2, MGM-9, EN-3231, NRP-290, NS-7051, CDS-PM-101, frakefamide, BCH-2687, SS-620, VANH-36, 443C81, OHM-329, dermorphin tetrapeptide analogue, sameridine, OHM-3507, SEP-130551, BW-2378W92, sulfazocine, Z-4349, RP-63494, BCH-150, CP-840, and CP-0719.

9. The method according to claim 1, wherein the pain is selected from the group consisting of acute pain and chronic pain, and the chronic pain is selected from the group consisting of headache, maxillofacial pain, cervical and occipital pain, neck and shoulder pain, upper limb pain, chest pain, abdominal pain, lumbocrural pain, genital tract pain, urinary tract pain and dysmenorrhea.

10. The method according to claim 1, wherein the pain is selected from the group consisting of traumatic pain, inflammatory pain, ischemic pain, pain caused by metabolic diseases, neuropathic pain, pain caused by tissue and organ malformation, labor pain and pain caused by malignant proliferative diseases; the traumatic pain is selected from the group consisting of pain caused by surgery, fracture pain, burn pain, abdominal traumatic pain, spinal traumatic pain, chest traumatic pain and post-traumatic headache; the inflammatory pain is selected from the group consisting of inflammatory headache, tissue inflammatory pain, organ and gland inflammatory pain and vascular inflammatory pain; the ischemic pain is selected from the group consisting of ischemic headache, limb ischemic pain, tissue ischemic pain, and organ and gland ischemic pain; the pain caused by metabolic diseases is selected from the group consisting of pain caused by gout and pain caused by diabetes; the neuropathic pain is selected from the group consisting of phantom limb pain, stump pain, burning neuralgia, postherpetic neuralgia, sympathetic-related pain, pain caused by burning foot syndrome, folic acid deficiency peripheral neuralgia, vitamin B12 deficiency peripheral neuralgia, vitamin B1 deficiency multiple neuralgia and leprosy neuralgia; the pain caused by malignant proliferative diseases is pain caused by tumors.

11. The method according to claim 10, wherein the pain is a moderate to severe pain selected from the group consisting of traumatic pain, labor pain, pain caused by tumors and inflammatory pain.

12. The method according to claim 11, wherein the moderate to severe pain is not sensitive to non-opioid analgesics.

13. The method according to claim 1, wherein the combination further comprises a third component selected from the group consisting of an opioid, glucocorticoid, non-steroidal anti-inflammatory drug, anesthetic, local anesthetic, anti-depressant, calcium channel antagonist, anti-convulsant, adrenal beta receptor blocker, and anesthesia inducer.

14. A pharmaceutical composition, comprising a MOR agonist and a KOR agonist, and one or more pharmaceutically acceptable excipients, diluents or carriers, wherein the KOR agonist is a compound of formula (I):

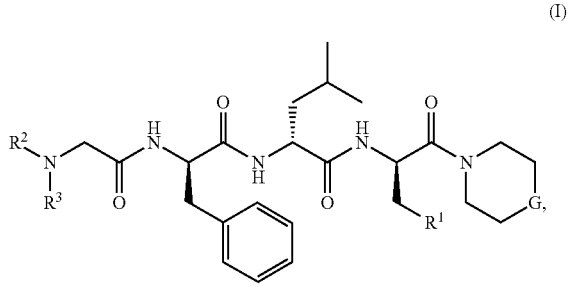

or a tautomer, mesomer, racemate, enantiomer, or diastereomer thereof, or a mixture thereof, or a pharmaceutically acceptable salt thereof, wherein:

G is selected from the group consisting of O, —NR$^4$ and —CR$^5$R$^6$;

R$^1$ is selected from the group consisting of hydrogen, alkyl, alkoxy, haloalkyl, halogen, amino, nitro, hydroxy, cyano, cycloalkyl, heterocyclyl, aryl, heteroaryl, —OR$^7$, —C(O)R$^7$, —C(O)OR$^7$, —S(O)$_m$R$^7$ and —NR$^8$R$^9$, wherein the alkyl, haloalkyl, cycloalkyl, heterocyclyl, aryl and heteroaryl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

R$^2$ is selected from the group consisting of hydrogen, alkyl, alkoxy, haloalkyl, cycloalkyl, cycloalkylalkyl, heterocyclyl, heterocyclylalkyl, aryl, arylalkyl, heteroaryl, heteroarylalkyl, —OR$^7$, —C(O)R$^7$ and —C(O)OR$^7$, wherein the alkyl, haloalkyl, cycloalkyl, cycloalkylalkyl, heterocyclyl, heterocyclylalkyl, aryl, arylalkyl, heteroaryl and heteroarylalkyl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

R$^3$ is selected from the group consisting of hydrogen, alkyl, alkoxy, haloalkyl, cycloalkyl, cycloalkylalkyl, heterocyclyl, heterocyclylalkyl, aryl, arylalkyl, heteroaryl, heteroarylalkyl, —OR$^7$, —C(O)R$^7$ and —C(O)OR$^7$, wherein the alkyl, haloalkyl, cycloalkyl, cycloalkylalkyl, heterocyclyl, heterocyclylalkyl, aryl, arylalkyl, heteroaryl and heteroarylalkyl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

R$^4$ is selected from the group consisting of hydrogen, alkyl, haloalkyl, cycloalkyl, alkoxy, hydroxyalkyl, amino, alkoxycarbonyl, heterocyclyl, aryl, heteroaryl, —OR$^7$, —C(O)R$^7$, —C(O)OR$^7$, —S(O)$_m$R$^7$, —NR$^8$R$^9$ and —NHC(O)NR$^8$R$^9$, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, hydroxyalkyl, cycloalkyl, heterocyclyl, aryl and heteroaryl;

R$^5$ and R$^6$ are each independently selected from the group consisting of hydrogen, alkyl, alkoxy, hydroxyalkyl, hydroxy, amino, alkoxycarbonyl, cycloalkyl, heterocyclyl, aryl, heteroaryl, —OR$^7$, —C(O)R$^7$, —C(O)OR$^7$, —S(O)$_m$R$^7$, —NR$^8$R$^9$ and —NHC(O)NR$^8$R$^9$, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

R$^7$ is selected from the group consisting of hydrogen, alkyl, amino, alkoxy, hydroxyalkyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, nitro, cyano, hydroxyalkyl, cycloalkyl, heterocyclyl, aryl and heteroaryl;

R$^8$ and R$^9$ are each independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl; and m is 0, 1 or 2;

and wherein the MOR agonist is a compound of formula (II):

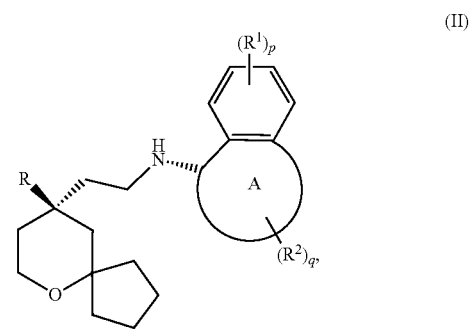

or a tautomer, mesomer, racemate, enantiomer, diastereomer thereof, or mixture thereof, or a pharmaceutically acceptable salt thereof, wherein:

ring A is selected from the group consisting of cycloalkyl and heterocyclyl;

R is selected from the group consisting of aryl and heteroaryl, wherein the aryl and heteroaryl are each optionally substituted by one or more substituents selected from the group consisting of alkyl, haloalkyl, halogen, amino, nitro, cyano, alkoxy, haloalkoxy, hydroxyalkyl, cycloalkyl, heterocyclyl, aryl, heteroaryl, —OR$^3$, —C(O)R$^3$, —C(O)OR$^3$, —S(O)$_m$R$^3$ and —NR$^4$R$^5$;

each R$^1$ is identical or different and each is independently selected from the group consisting of hydrogen, alkyl, alkoxy, haloalkyl, halogen, amino, nitro, hydroxy, cyano, cycloalkyl, heterocyclyl, aryl, heteroaryl, —OR$^3$, —C(O)R$^3$, —C(O)OR$^3$, —S(O)$_m$R$^3$ and —NR$^4$R$^5$, wherein the alkyl, haloalkyl, cycloalkyl, heterocyclyl, aryl and heteroaryl are each optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

each R$^2$ is identical or different and each is independently selected from the group consisting of hydrogen, alkyl, alkoxy, haloalkyl, halogen, amino, nitro, hydroxy, cyano, oxo, alkenyl, cycloalkyl, heterocyclyl, aryl, heteroaryl, —OR$^3$, —C(O)R$^3$, —C(O)OR$^3$, —S(O)$_m$R$^3$ and —NR$^4$R$^5$, wherein the alkyl, alkoxy, alkenyl, haloalkyl, cycloalkyl, heterocyclyl, aryl and heteroaryl are each optionally substituted by one or more substituents selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl and heteroaryl;

or two R² are taken together to form a cycloalkyl or heterocyclyl, wherein the cycloalkyl or heterocyclyl is optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

R³ is selected from the group consisting of hydrogen, alkyl, deuterated alkyl, amino, alkoxy, hydroxyalkyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, nitro, cyano, alkoxy, hydroxyalkyl, cycloalkyl, heterocyclyl, aryl and heteroaryl;

R⁴ and R⁵ are each independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, cycloalkyl, heterocyclyl, aryl and heteroaryl are each optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

p and q are each independently 0, 1, 2, 3 or 4; and m is 0, 1 or 2.

15. The method according to claim 4, wherein the KOR agonist is

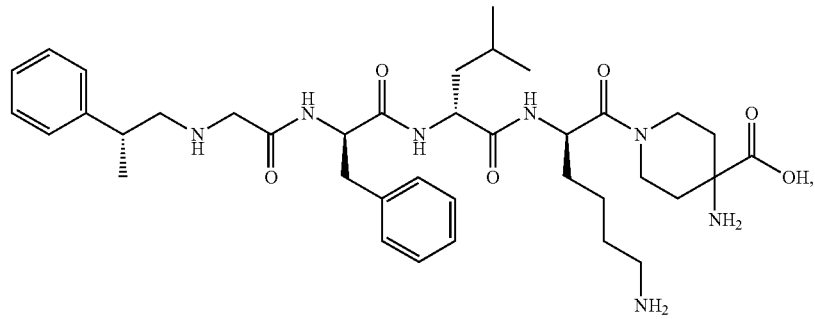

5 or a tautomer, mesomer, racemate, enantiomer, or diastereomer thereof, or a mixture thereof, or a pharmaceutically acceptable salt thereof.

16. The method according to claim 7, wherein the MOR agonist is

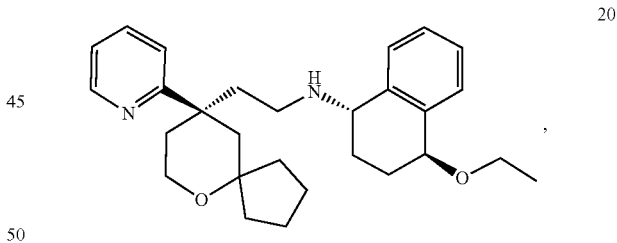

20 or a tautomer, mesomer, racemate, enantiomer, or diastereomer thereof, or a mixture thereof, or a pharmaceutically acceptable salt thereof.

17. The method according to claim 10, wherein the malignant proliferative disease is selected from the group consisting of leukemia, lymphoma, myeloma, breast cancer, lung cancer, esophageal cancer, stomach cancer, colorectal cancer, liver cancer, pancreatic cancer, head and neck cancer, kidney cancer, bladder cancer, prostate cancer, ovarian cancer, endometrial cancer, cervical cancer, osteosarcoma, soft tissue sarcoma, melanoma and brain tumor.

18. A method of alleviating and/or treating pain in a subject in need thereof, comprising administering to the subject a therapeutically effective amount of a pharmaceutical composition comprising a κ opioid receptor (KOR) agonist and a μ opioid receptor (MOR) agonist, wherein the KOR agonist is selected from the group consisting of:
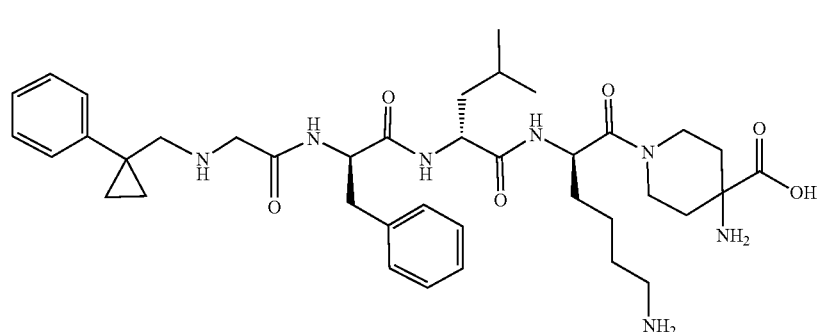
1
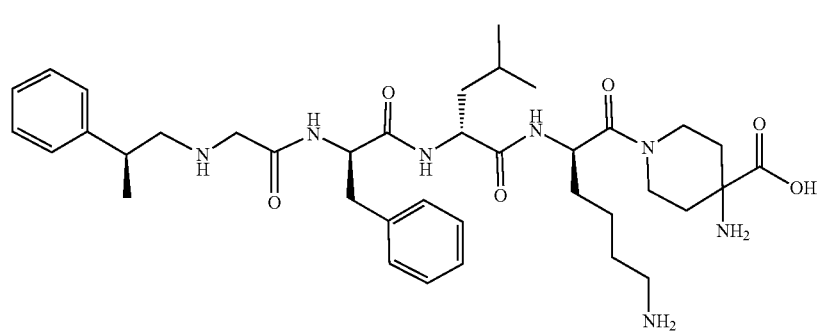
2
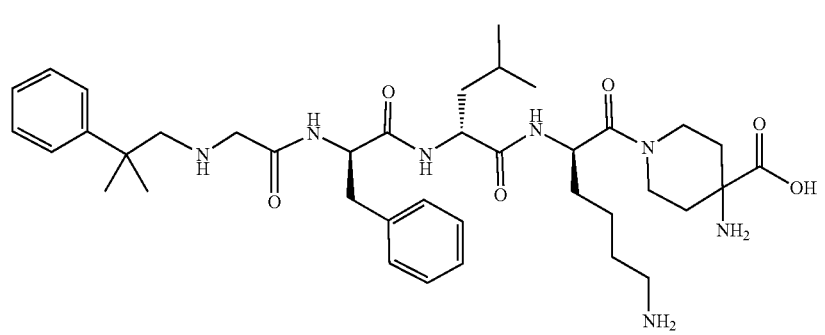
3
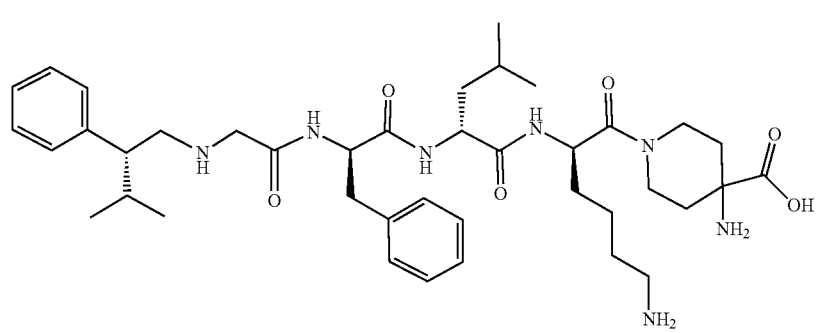
4
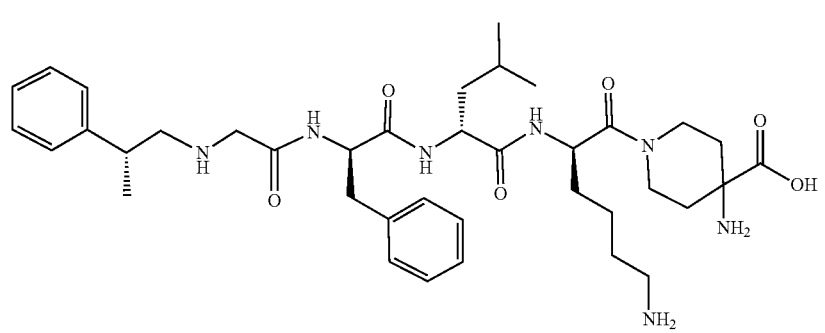
5

6
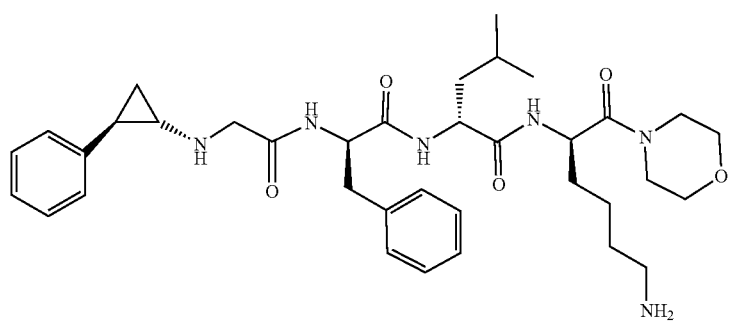
7
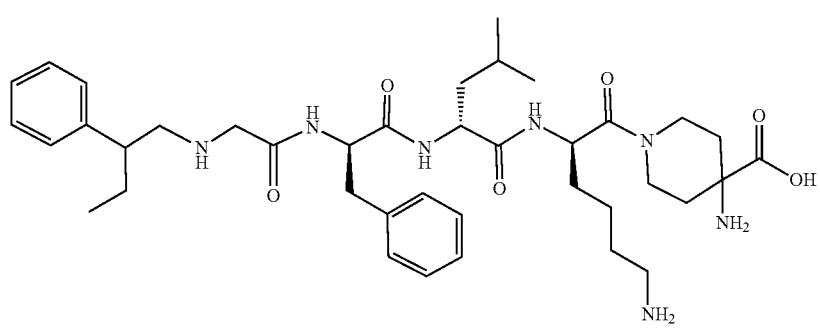
8
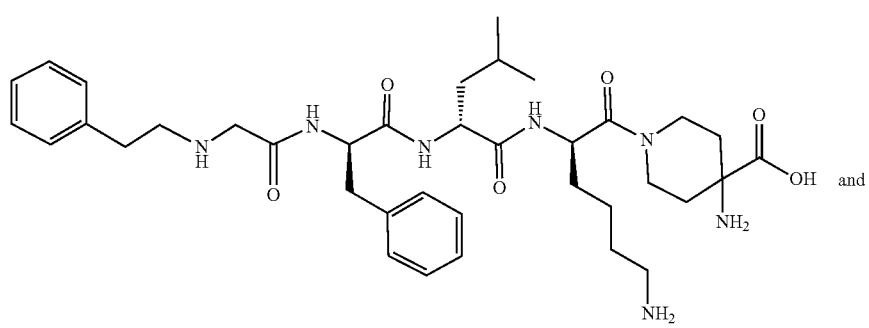
and
9
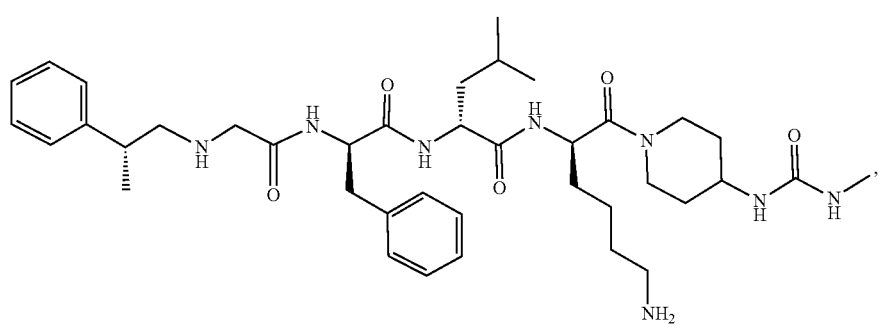

or a tautomer, mesomer, racemate, enantiomer, or diastereomer thereof, or a mixture thereof, or a pharmaceutically acceptable salt thereof, and
the MOR agonist is selected from the group consisting of:
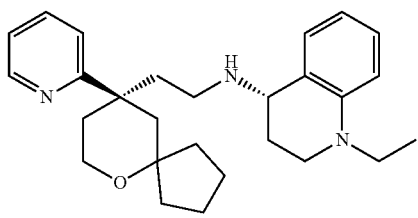
10
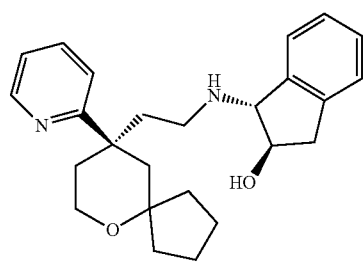
11
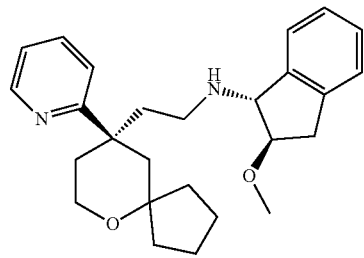
12
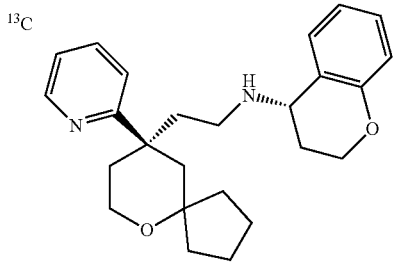
13
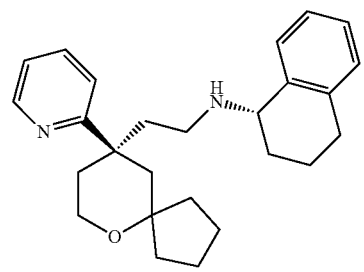
14
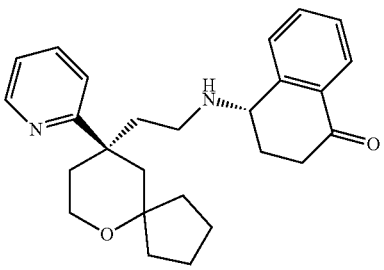
15
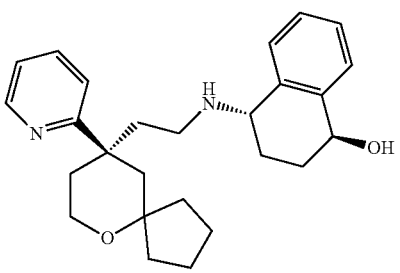
16
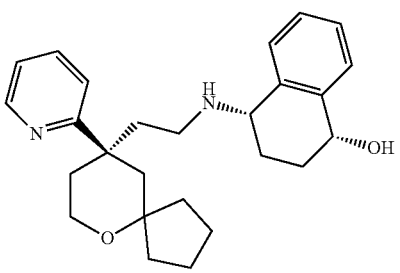
17
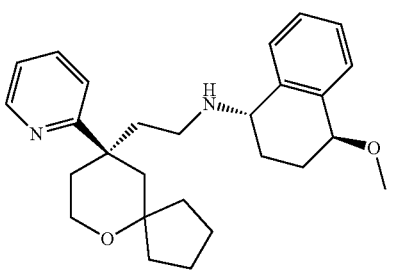
18
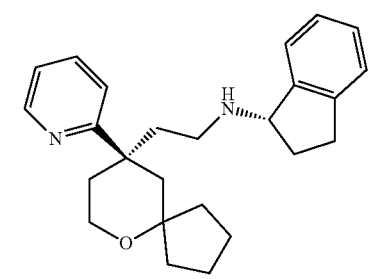
19
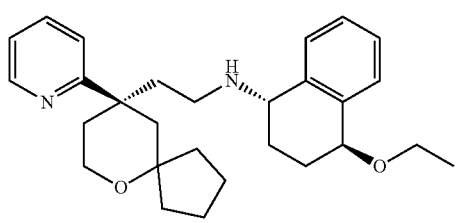
20

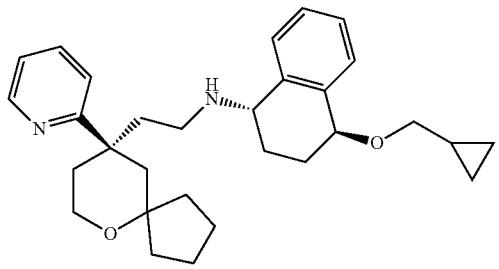
21
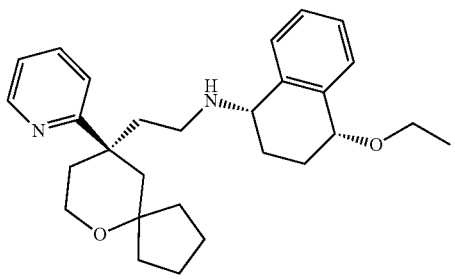
26
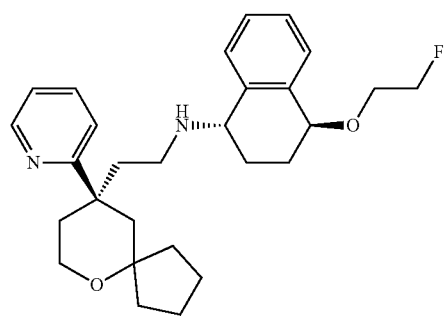
22
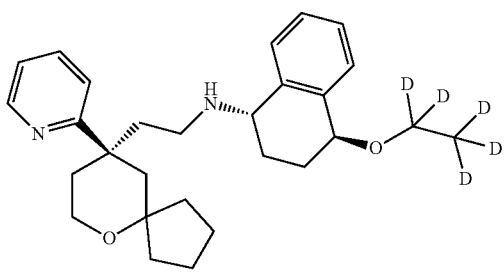
27
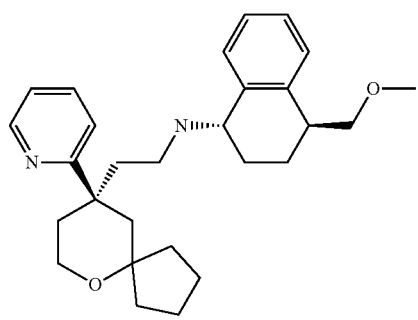
23
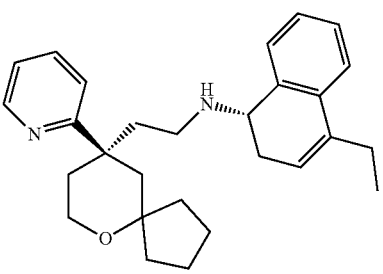
28
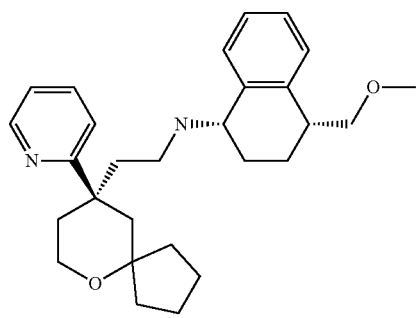
24
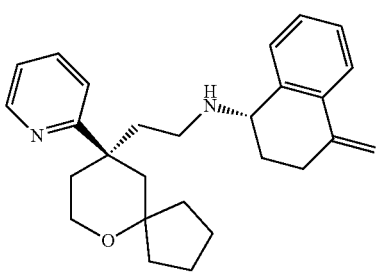
29
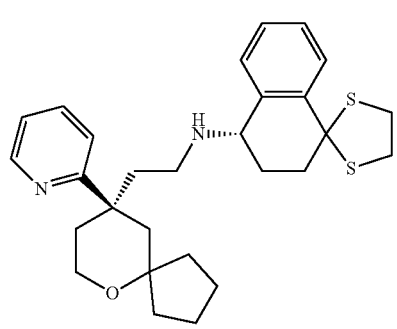
25
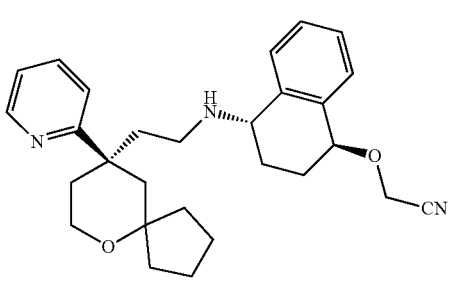
30

31
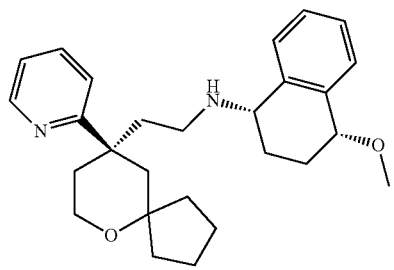
32
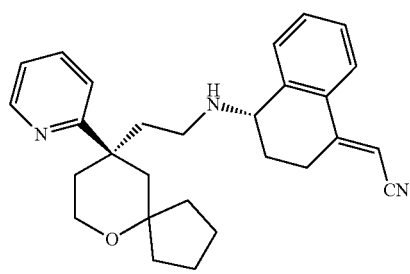
33
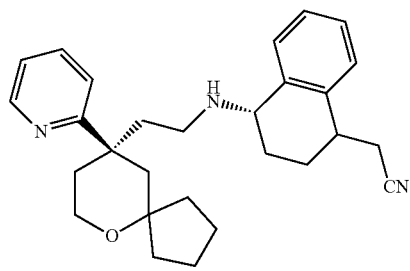
34
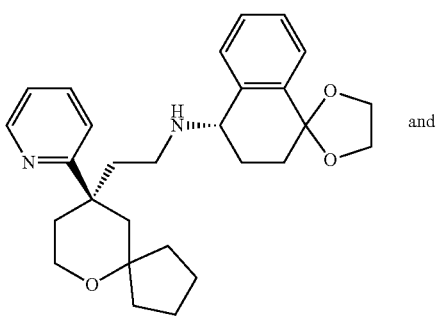
and
35
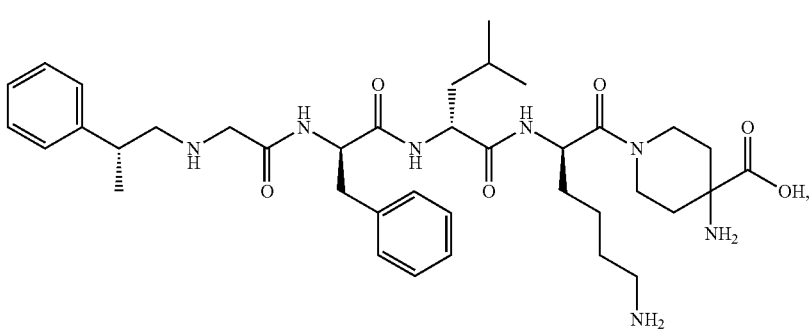
or a tautomer, mesomer, racemate, enantiomer, or diastereomer thereof, or a mixture thereof, or a pharmaceutically acceptable salt thereof.
19. The method according to claim 18, wherein the KOR agonist is
5 or a tautomer, mesomer, racemate, enantiomer, or diastereomer thereof, or a mixture thereof, or a pharmaceutically acceptable salt thereof, and the the MOR agonist is

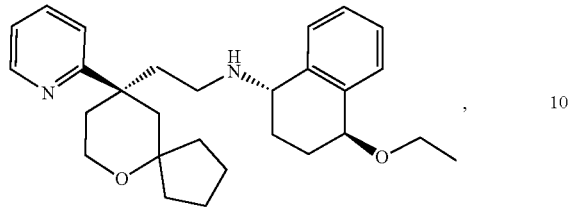

or a tautomer, mesomer, racemate, enantiomer, or diastereomer thereof, or a mixture thereof, or a pharmaceutically acceptable salt thereof.

20. The method according to claim 18, wherein the pain is selected from the group consisting of acute pain and chronic pain, and the chronic pain is selected from the group consisting of headache, maxillofacial pain, cervical and occipital pain, neck and shoulder pain, upper limb pain, chest pain, abdominal pain, lumbocrural pain, genital tract pain, urinary tract pain and dysmenorrhea.

* * * * *